US006767705B2

(12) United States Patent
Roninson et al.

(10) Patent No.: US 6,767,705 B2
(45) Date of Patent: Jul. 27, 2004

(54) REAGENTS AND METHODS FOR IDENTIFYING AND MODULATING EXPRESSION OF GENES REGULATED BY RETINOIDS

(75) Inventors: Igor B. Roninson, Wilmette, IL (US); Milos Dokmanovic, Chicago, IL (US); Bey-Dih Chang, Lombard, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 09/865,879

(22) Filed: May 25, 2001

(65) Prior Publication Data

US 2003/0180707 A1 Sep. 25, 2003

Related U.S. Application Data

(60) Provisional application No. 60/207,535, filed on May 26, 2000.

(51) Int. Cl.[7] .................................................. C12Q 1/68
(52) U.S. Cl. .................................... 435/6; 435/7; 435/8
(58) Field of Search ........................... 435/4, 6, 7.1, 7.2, 435/7.21, 29, 8; 536/23.5

(56) References Cited

U.S. PATENT DOCUMENTS

| 5,444,164 A | | 8/1995 | Purchio et al. | |
|---|---|---|---|---|
| 5,795,726 A | * | 8/1998 | Glucksmann | .................. 435/4 |
| 5,965,382 A | | 10/1999 | Koths et al. | |

FOREIGN PATENT DOCUMENTS

| EP | 0 280 135 A | 8/1988 |
|---|---|---|
| WO | WO 91 14695 A | 10/1991 |
| WO | WO 91/14695 A | 10/1991 |
| WO | WO 93/06835 A | 4/1993 |
| WO | WO 96/23080 A | 8/1996 |
| WO | WO 96 23080 A | 8/1996 |
| WO | WO 98 08546 A | 3/1998 |
| WO | WO 98/08546 A | 3/1998 |
| WO | WO 98/23747 A | 6/1998 |
| WO | WO 98/31701 A | 7/1998 |
| WO | WO 00/09657 A | 2/2000 |
| WO | WO 00/29437 A | 5/2000 |
| WO | WO 01/15520 A | 3/2001 |
| WO | WO 01/18019 A | 3/2001 |

OTHER PUBLICATIONS

Kim et al, Oncogene. Apr. 3, 2003;22(13):2045–53.*
Darnell et al (Molecular Cell Biology, 1990, W. H. Freeman and Company, p. 344 only).*
Montemurro et al (1999, British Journal of Haematology, vol. 107, pp. 294–299, abstract only).*
Genbank Accession No. M35878.*
Miller (1998, Cancer 83: 1471–82).*
Han et al (1997, J. Biol. Chem. 272: 13711–13716).*
Adamo et al (1992, Endocrinology 131:1858–1866).*
Cohick et al (1998, Journal of Endocrinology 157: 327–336).*
Ming et al., "Expression genetics: a different approach to cancer diagnosis and prognosis", Trends in Biotechnology, Elsevier Publications, Cambridge, GB, vol. 16, No. 2, Feb. 1, 1998, pp. 66–71.

(List continued on next page.)

Primary Examiner—Larry R. Helms
Assistant Examiner—Misook Yu
(74) Attorney, Agent, or Firm—McDonnell Boehnen Hulbert & Berghoff

(57) ABSTRACT

This invention identifies growth-inhibitory genes induced by retinoids. The invention provides reagents and methods for identifying compounds other than retinoids that induce expression of these cellular genes. The invention also provides reagents that are recombinant mammalian cells containing recombinant expression constructs that express a reporter gene under the transcriptional control of a promoter for a gene that is regulated by retinoids, and methods for using such cells to identify compounds other than retinoids that modulate expression of these cellular genes.

4 Claims, 3 Drawing Sheets

OTHER PUBLICATIONS

Huang et al. "Cloning and Characterization of a Novel Retinoid–Inducible Gene 1 (RIG1) Deriving from Human Gastric Cancer Cells" Molecular and Cellular Endocrinology, Amsterdam, Netherlands, vol. 159, No. 1/2, Jan. 25, 2000, pp. 15–24.

Kumar et al., "Setting up Reporter–Gene Based Assay Systems for Screening Antineoplastic Drugs", Pharmaceutical Technology, Jun. 1, 1991, pp. 39–43.

Dokmanovic et al., "Molecular basis of senescence—like growth arrest induced in breast carcinoma cells by retinoids" Proceedings of the American Association for Cancer Research Annual., vol. 42, Mar. 2001, p. 210.

Dokmanovic et al., "Retinoid–induced growth arrest of breast carcinoma cells involves co–activation of multiple growth–inhibitory genes" Cancer Biology & Therapy, Jan.–Feb. 2002 vol. 1, No. 1, Jan. 2002 pp. 24–27.

Cubbage et al., "Insulin–like Growth Factor Binding protein–3", Journal of Biological Chemistry, vol. 265, No. 21, Jul. 15, 1990, 12642–12649.

Hembree et al., "Retinoid X Receptor–Specific Retinoids Inhibit the Ability of Retinoic Acid Receptor–Specific Retinoids to Increase the Level of Insulin–Like Growth Factor Binding Protein–3 in Human Ectocervical Epithelial Cells", Cancer Research vol. 56, No. 8, Apr. 15, 1996, pp. 1794–1799.

Shang et al., "Signal relay by retinoic acid receptors alpha and beta in the retinoic acid–induced expression of insulin–like growth factor–binding protein–3 in breast cancer cells", Journal of Biological Chemistry, vol. 274, No. 25, Jun. 18, 1999, pp. 18005–18015.

Han et al., "All–trans–retinoic acid increases transforming growth factor–beta–2 and insulin–like growth factor binding protein–3 expression through a retinoic acid receptor–alpha–dependent signaling pathway", Journal of Biological Chemistry, vol. 272, No. 21, 1997, pp. 13711–13716.

Simon et al., "Effect of PD 098059, a specific inhibitor of mitogen–activated protein kinase kinase, on urokinase expression and in vitro invasion", Cancer Research, vol. 56, No. 23, 1996, pp. 5369–5374.

Albiston et al., "Cloning and characterization of the promoter for the rat insulin–like growth factor–binding protein–3 gene" Endocrinology, vol. 136, No. 2, 1995, pp. 696–704.

Heller et al., "Transcriptional regulation of the Bmp2 gene. Retinoic acid induction in F9 embyonal carcinoma cells and *Saccharomyces cerevisiae*", Journal of Biological Chemistry, vol. 274, No. 3, Jan. 15, 1999, pp. 1394–1400.

Skonier et al., "CDNA Cloning and Sequence and Analysis of Beta–ig–h3, a novel gene induced in a human adenocarcinoma cell line after treatment with transforming growth factor–beta", DNA and Cell Biology, vol. 11, No. 7, 1992, pp. 511–522.

Skonier et al., "Betaig–H3: A Transforming Growth Factor–Beta–Responsive Gene Encoding A Secreted Protein That Inhibits Cell Attachment in Vitro and Suppresses the Growth of Cho Cells in Nude Mice", DNA and Cell Biology, New York, NY, vol. 13, No. 6, 1994, pp. 571–584.

Tsujimoto et al. "Differential gene expression in tumorigenic ans nontumorigenic HeLa x normal human fibroblast hybrid cell", Molecular Carcinogenesis, vol. 26, No. 4, Dec. 1999, pp. 298–304.

Schenker et al.,"Down–regulated proteins of Mesenchymal tumor cells" Experimental Cell Research, vol. 239, No. 1, Feb. 25, 1998, pp. 161–168.

DATABASE GenBank NCBI; Mar. 30, 1998 AC004503.

Hu et al.,"Profiling of differentially expressed cancer–related genes in esophageal squamous cell carcinoma (ESCC) using human cancer cDNA arrays: overexpression of oncogene MET correlates with tumor differentiation in ESCC" Clinical Cancer Research: An Official Journal of the American Association for Cancer Research, Nov. 2001, vol. 7, No. 11, Nov. 2001, pp. 3519–.

Chen et al., "Characterization of the human EPLIN gene reveals distinct promoters for the two EPLIN isoforms" Gene vol. 248, No. 1–2, May 2, 2000, pp. 69–76.

Maul et al., Eplin, Epithelial Protein Lost in Neoplasm Oncogene, vol. 18, 1999, pp. 7838–7841.

Yuan–Ching et al., "A MHC–encoded ubiquitin–like protein (FAT10) binds noncovalently to the spindle assembly checkpoint protein MAD2" Proceedings of the National Academy of Sciences of the United States, vol. 96, No. 8, Apr. 13, 1999, pp. 4313–4318.

Raasi et al., "A ubiquitin–like protein which is synergistically inducible by interferon–gamma and tumor necrosis factor–alpha", European Journal of Immunology, Germany, Dec. 1999, vol. 29, No. 12, pp. 4030–4036.

DATABASE EMBL Online, Oct. 27, 1998, Database Accession No. AL031983.

RAASI et al., "The ubiquitin–like protein FAT10 forms covalent conjugates and induces apoptosis", Journal of Biological Chemistry, vol. 276, No. 38, Sep. 21, 2001 pp. 35334–35343.

DATABASE EMBL Online, Jan. 11, 2000, Database Accession No. AL136295.

Frisan et al., "Variations in proteasome subunit composition and enzymatic activity in B–lymphoma lines and normal B cells." International Journal of Cancer, vol. 88, No. 6, 2000, pp. 881–888.

Groettrup et al., "A role for the proteasome regulator PA28–alpha in antigen presentation.", Nature (London), vol. 381, No. 6578, 1996, pp. 166–168.

Delp et al, "Functional deficiencies of components of the MHC class I antigen pathway in human tumors of epithelial origin", Bone Marrow Transplatation, vol. 25, No. Supplement 2, May 2000, pp. S88–S95.

Wojcik and Wilk, "Changes in proteasome expression and activity during differentiaion of neuronal precur Ntera 2 clone D1 cells", Neutochemistry International, vol. 34, 1999, pp. 131–136.

Ritz et al., "Deficient expression of components of the MHC class I antigen processing machinery in human cervical carcinoma." International Journal of Oncology, vol. 19, No. 6, Dec. 2001, pp. 1211–1220.

Brakebusch et al., "Isolation and functional Characterization of the Human 90K promoter." Genomics, vol. 57, No. 2, Apr. 15, 1999, pp. 268–278.

Chang et al., "Effects of p21WAF1/CIP1/SDI1 on Cellular Gene Expression: Implications for Carginogenesis, Senescence, and Age–Related Diseases" Proceedings of the National Academy of Sciences of USA, National Academy of Science. Washington, US. vol. 97, No. 8, Apr. 2000, pp. 4291–4296.

Brakebusch et al., "Expression of the 90K immunostimulator gene is controlled b a promoter with Unique Features" Journal of Biological Chemistry, vol. 272, No. 6, 1997 pp. 3674–3682.

Marchetti Antonio et al: "Expression of 90K (Mac–2 BP) correlates with distant metastasis and predicts survival in stage I non–small cell lung cancer patients." Cancer Research, May 1, 2002, vol. 62, No. 9, pp. 2535–2539.

Hayashi et al., "Regulation of the human protein C inhibitor gene expression in HepG2 cells: role of Sp1 and AP2", The Biochemical Journal, Jun. 1, 1998, vol. 332, Jun. 1, 1998.

Suzuki et al. "Protein C inhibitor (PAI–3): Structure and multi–function." Fibrinolysis & Proteolysis, vol. 14, No. 2–3, Mar. 2000, pp. 133–145.

DATABASE EMBL Online EBI; Nov. 15, 1999, Accession No. AL132990.

Hettmann et al., "The Human T Cell Receptor Gamma Genes are Transcribed from Tata–less Promoters Containing a Conserved Heptamer Sequence", Molecular Immunology, vol. 29, No. 9, 1992, pp. 1073–1080.

DATABASE EMBL 'Online' Nov. 23, 1989 Accession No. X15274.

Essand et al., High expression of a specific T–cell receptor gamma transcript in epithelial cells of the prostate:, Proceedings of the National Academy of Science, vol. 96, Aug. 1999, pp. 9287–9292.

Wright et al., "Molecular Cloning, refined chromosomal mapping and structural analysis of the human gene encoding aldehyde oxidase (AOX1), a candidate for the ALS2 gene", Redox Report, vol. 3, 1997, pp. 135–144.

Terao et al., "Isolation and characterization of the human aldehyde oxidase gene: conservation of intron/exon boundaries with the xanthine oxidoreductase gene indicates a common origin", The Biochemical Journal, England, Jun. 1, 1998, vol. 332.

Tomita et al., "Retinal oxidase is identical to aldehyde oxidase", FEBS Letters, vol. 336, No. 2, 1993, pp. 272–274.

Sato et al., "Changes of gene expression by lysophosphatidylcholine in vascular endothelial cells: 12 Up–regulated distinct genes including 5 cell growth–related, 3 thrombosis–related, and 4 others.", Journal of Biochemistry, vol. 123, No. 6, Jun. 1998, pp. 1119–1126.

Lautner–Rieske et al., "Searching for non–Vkappa transcripts from the human immunoglobulin kappa locus", Gene, Elsevier Biomedical Press., Amsterdam, NL. vol. 159, No. 2, Jul. 4, 1995, pp. 199–202.

DATABASE Genbank, Shimizu and Kawasaki, "*Homo sapiens* genomic DNA, chromosome 2p11.2, clone:cos607/4", Accession No. AP001234.

Del Carmen De Marco Maria et al. "Bene, a novel raft–associated protein of the MAL proteolipid family, interacts with caveolin–1 in human endothelial–like ECV304 cells" Journal of Biological Chemistry, vol. 276, No. 25, Jun. 22, 2001, pp. 23009–23017.

Wiesener et al., "Induction of endothelial PAS domain protein–1 by hypoxia: Characterization and comparison with hypoxia–inducible factor–alpha", Blood, vol. 92, No. 7, Oct. 1, 1998, pp. 2260–2268.

DATABASE EMBL "Online" Dec. 14, 1999, Sulston: "*Homo sapiens* BAC clone RP11–130P22 form 2, complete sequence", Accession No. AC016696.

Dang et al., "Oncogenes in Tumor Metabolism, Tumorigenesis, and Apoptosis", Journal of Bioenergetics and Biomembranes, plenum publishing, New York, NY, US, vol. 29, No. 4, Aug. 1997, pp. 345–354.

Feldser et al., "Reciprocal positive regulation of hypoxia–inducible factor 1alpha and insulin–like growth factor 2", Cancer Research, American Association for Cancer Research, vol. 59, Aug. 15, 1999, pp. 3915–3918.

Blancher et al., "The Molecular Basis of the Hypoxia response Pathway: Tumour hypoxias a therapy target", Cancer Metastasis, vol. 17, 1998, pp. 187–194.

Talks et al., "The expression and distribution of the hypoxia–inducible factors HIF–1alpha and HIF–2alpha in normal human tissues, cancers, and tumor–associated macrophages." American Journal of Pathology, Aug. 2000, vol. 157, No. 2, Aug. 2000, pp. 411–421.

Ord et al., "Structure of the Gene Encoding the Human Leukocyte Adhesion Molecule–1 TQ1 LEU–8 of Lymphocytes and Neutrophils", Journal of Biological Chemistry, vol. 265, No. 14, 1990, pp. 7760–7767.

DATABASE Biosis "Online" Biosciences Information Service, Philadelphia, PA, Feb. 2000, Accession No. PREV200000177491 XP002224066.

Tatewaki et al., "Constitutive overexpression of the L–selectin gene in fresh leukemic cells of adult T–cell leukemia that can be transactivated by human T–cell lymphotropic virus type 1 Tax." Blood, United States, Oct. 15, 1995, pp. 3109–3117.

Qian et al., "L–selectin can facilitate metastasis to lymph nodes in a transgenic mouse model of carcinogenesis." Proceedings of the National Academy of Sciences of the United States, vol. 98, No. 7, Mar. 27, 2001, pp. 3976–3981.

Adamo et al., Endocrinology 131:1858–1866.

Chang et al., 1999, Cancer Res. 59:3761–3767.

DiSepio et al., 1998, Proc. Natl. Acad. Sci. USA 95:14811–14815.

Gucev et al., 1996, Cancer Res. 56:1545–1550.

Hayflick and Moorhead, 1961, Exp. Cell. Res. 25:585–621.

Huang et al., 2000, Molec. Cell. Endocrinol. 159:15–24.

Kato et al., 1996, Oncogene 12:1361–1364.

Liu et al., 2000 J. Cancer Res. Clin. Oncol. 126:85–90.

Miller et al., 1998, Cancer 83:1471–1482.

Noonan et al., 1990, Proc. Natl. Acad. Sci. USA 87:7160–7164.

Sugrue et al., 1997, Proc. Natl. Acad. Sci. USA 94:9648–9653.

Swisshelm et al., 1995, Proc. Natl. Acad. Sci. USA 92:4472–4476.

Uhrbom et al., 1997, Oncogene 15:505–514.

Vogt et al., 1998, Cell Growth Differ. 9:139–146.

Xu et al., 1997, Oncogene 15:2589–2596.

Zhu et al., 1997, Exp. Cell Res. 234:293–299.

Cubbage et al., "Insulin–like Growth Factor Binding protein–3", Journal of Biological Chemistry, vol. 265, No. 21, Jul. 15, 1990, 12642–12649.

Hembree et al., "Retinoid X Receptor–Specific Retinoids Inhibit the Ability of Retinoic Acid Receptor–Specific Retinoids to Increase the Level of Insulin–Like Growth Factor Binding Protein–3 in Human Ectocervical Epithelial Cells", Cancer Research vol. 56, No. 8, Apr. 15, 1996, pp. 1794–1799.

Shang et al., "Signal relay by retinoic acid receptors alpha and beta in the retinoic acid–induced expression of insulin–like growth factor–binding protein–3 in breast cancer cells", Journal of Biological Chemistry, vol. 274, No. 25, Jun. 18, 1999, pp. 18005–18015.

Han et al., "All–trans–retinoic acid increases transforming growth factor–beta–2 and insulin–like growth factor binding protein–3 expression through a retinoic acid receptor–alpha–dependent signaling pathway", Journal of Biological Chemistry, vol. 272, No. 21, 1997, pp. 13711–13716.

Simon et al., "Effect of PD 098059, a specific inhibitor of mitogen–activated protein kinase kinase, on urokinase expression and in vitro invasion", Cancer Research, vol. 56, No. 23, 1996, pp. 5369–5374.

Kumar et al., "Setting up Reporter–Gene Based Assay Systems for Screening Anineoplastic Drugs" Pharmaceutical Technology, Jun. 1, 1991, pp. 39–43.

Albiston et al., "Cloning and chracterization of the promoter for the rat insulin–like growth factor–binding protein–3 gene" Endocrinology, vol. 136, No. 2, 1995, pp. 696–704.

Heller et al., "Transcriptional regulation of the Bmp2 gene. Retinoic acid induction in F9 embyonal carcinoma cells and *Saccharomyces cerevisiae*", Journal of Biological Chemistry, vol. 274, No. 3, Jan. 15, 1999, pp. 1394–1400.

* cited by examiner

SEQUENCE LISTING

<160> NUMBER OF SEQ ID NOS: 44

<210> SEQ ID NO 1
<211> LENGTH: 1806
<212> TYPE: DNA
<213> ORGANISM: Homo sapiens
<220> FEATURE:
<221> NAME/KEY: misc_feature
<223> OTHER INFORMATION: IGFBP-3 NCBI acc. number : M35878.1

<400> SEQUENCE: 1

```
ggggattcgt tttgtttcct tcaatttcc aatgaaatca gagatcctgt tcttgggtgt      60
caacgcagat actagaagga ggtgatacaa gagaaaggaa cagcaagcga cgattatggc     120
acggtttcct gtaaacaagg ttgagtgtag ccacagcctg agcactgtgg gagaagagct     180
cataagaaaa tgacggtgct gggccttcgt cacccggggg ccctccattg ttcttgtctt     240
tggtctcttt ttatttgtag aggtccaatt atttatttat ttagtacaag agggaacgaa     300
attgatcttt ccattctaaa aggagagtat atatgtataa aaggaagctg tatagatatg     360
ggggaagagg tggacagggg gaaaagggga gaggacgaga gagagaaagg gagggagagg     420
gacaaggaga gacactgggc gagagatcga ttaggagaga cagaaatgat gaatgaagat     480
taacttcacc caaggcttcg tcgctggagg ggaatggagg agctcctgat ttgctattac     540
tactccaaac tgcaaagggc tccttcaagt cacctatcca cctcctaagg caagcgtcca     600
atttcaacag cgttcaggaa agtctcctcc cgcggaggtc tcaccgcttc ccactccacc     660
```

```
cccacaaact ctttggaaaa gtgccttgaa aaatttaatc ctcaatccaa tcctggacca    720
ccagcgtcct ctgttggtca ccgaaggagg gggtgcgcag acaaaactga agaaactcga    780
gtgccagaga aggccgacag gagttacagc gacctcagcg cgcaattgcg ccccgaactt    840
tactgaaaag tgtttagatt gcagagataa gctagaatcc caacgcatcg agaatacagt    900
aatacgaagt cgccttcaaa aaatgacaat gaaaattgcc tattaaagga ctatttggtt    960
aattacgttt cagcagtgcc cagtttattg tctttattat tcttttgtcg tgggtgtaaa   1020
ctccatttga aaacataatc agggagaata cccaagacaa gaagaacagt tgtcatttaa   1080
aatatttgaa aagccctgcc ttaaggagca ttcgcttgcc ggtccactct taattgggga   1140
cttgcggtgt agcaacacgt gagagtcttc ttgcgttgag aagtaagcct ggaaaggcga   1200
aggcccgggg gcatcttcag atgcgtattt gtgggcccct ggggatataa acagcccagc   1260
gggtgtaaat taaaccccgc agtgccttgg ctccctgaga cccaaatgta agtcagaaat   1320
gtcccaagac ttcgcctgcc aacgaattaa aattttagaa agctccacga ggtacacacg   1380
aatgcggagc gctgtatgcc agtttccccg acaccggctc gccgcaggga gacctcaccc   1440
cgagagcgga aggggtaagg gcggcggggt caaggagatc ggggggtgctg agttggccag   1500 gagtgactgg ggtgaccggg ggtgctgagg tggcctggag tgccggggtg gccgggcaca   1560
ccttggttct tgtagacgac aaggtgacgg gctccgggcg tgagcacgag gagcaggtgc   1620
ccgggcgagt ctcgagctgc acgcccccga gctcggcccc ggctgctcag ggcgaagcac   1680
gggccccgca gccgtgcctg cgccgacccg ccccctccc  aacccccact cctgggcgcg   1740
cgttccgggg cgtgtcctgg gccacccccgg cttctatata cgggccggcg cgcccgggcc   1800
gcccag                                                               1806
```

<210> SEQ ID NO 2
<211> LENGTH: 1553
<212> TYPE: DNA
<213> ORGANISM: Homo sapiens
<220> FEATURE:
<221> NAME/KEY: misc_feature
<223> OTHER INFORMATION: Beta IG-H3 promoter NCBI acc. number AC004503.1

<400> SEQUENCE: 2

```
gactcagggt gtcccaaacc actcatctac ctggcaagcc tgcactctgc atgtgcctca     60
ttctgaacat ggcaccatca ctgctgcaat gtccagacca caaacaccct acaatatcct    120
tgactctcct ttctcccctt ctccctgtat acagactcca aattctattg agactattac    180
ctcctacacc cctcacattt gcccagcctt ccccatctct gcctctacca ccatagttca    240
agctctccca tggtcccttc ctggttacct gttcttcttg cctccttaag cctctcatga    300
cactggccat gtcacttgcc tccacccatc acccgctagg ctcttagctg gagtctgggc    360
cctgctacct tcctcccctt cttccctacc cttgactcca cctccctgtg cttcagccaa    420
ccagataact tgagtttcgt gaatgcatgc ctcagtttac ctgattaact cattttcatc    480
tttcaggcct cagagcaggt atcaccctgt cagggccagg tgcctcttct tagctcccaa    540
agccccagct actcttcatg gaacatcatt ggcttgggct acggatcttc ccaaattgga    600 gcttttttcac aaagggctta ggtctcactc attctattaa tccatctgtg tctccccagg    660
gctagcagtg ccaagtaact gacaggtgat taatagatgc ttgggtaagt atcacctctt    720
taccatgtga caatttgttt acctgccttg agctcctcca gggcaggact cttgcctttg    780
cagaatctat ctggcaggta ctgttgcaga gatgtttact gaagaaggga atgaattagt    840
```

-continued

| | |
|---|---|
| accaaggtga ggaccccacc cttccccacg ggctccaaaa gcagcttaga gcccaacaaa | 900 |
| acctgcccca cattttttggc gtttctgtgg atcacacgat ttactcatct gtctttcaat | 960 |
| gagcatgaca ggtggggtgg gggtggaggg attagagatt gaggagctgg ggagggtggt | 1020 |
| cagctcctgg ggtgcagaaa caagtctgat gggccatggt gttctgggaa tcagcactgc | 1080 |
| ctcccctcac ccctccctgc agtgttttgt agcctcaaga tcagtgaggg aatcttcggg | 1140 |
| cccccagcat gcaggaccga agcccccgag acagctgtcc ctcagtccca aggtccccat | 1200 |
| ttggaagcag ccacaggagg cctaagggac ctatacccctt ggtttgagga agactgtggc | 1260 |
| gagggagaga gggagggagg gctggcagtg agggcaaggg ctgggaaaac tgagcacggg | 1320 |
| cacagtgcgg gagcgggtgg gtgcccaggg cagccagggg cgcacgggtt gggaggcgcc | 1380 |
| aggcggcccg ccctccttgc acgggccggc ccagcttccc cgcccctggc gtccgctccc | 1440 |
| tcccgctcgc agcttactta acctggcccg ggcggcggag gcgctctcac ttccctggag | 1500 |
| ccgcccgctt gcccgtcggt cgctagctcg ctcggtgcgc gtcgtcccgc tcc | 1553 |

<210> SEQ ID NO 3
<211> LENGTH: 840
<212> TYPE: DNA
<213> ORGANISM: Homo sapiens
<220> FEATURE:
<221> NAME/KEY: misc_feature
<223> OTHER INFORMATION: EPLIN beta promoter NCBI acc. number AH009382.1

<400> SEQUENCE: 3

| | |
|---|---|
| tggcatattc atcacctgtt ggaaatctct cttctcacac attttcatta acttcttgag | 60 |
| gaagtgtaat tacaagcgtt ttcccacgag cagcccctac taataacgca tcaagctgca | 120 |
| tgaattccga aaagcttcag aaaacttgtg gtctgaaacc ctactatgct tgaggtacag | 180 |
| gaaagaagga tactatcaaa aggcatcatg cagctggcac ggaactggga caagaatttg | 240 |
| ggggcaggat ggccaagtgc taggccaatt gacggtctcc aaaccattag cacagctcct | 300 |
| attctgaatg gaggagtaaa aacagctgtt ggagaacttg gacgtcatct gcccttgtca | 360 |
| aaccgttttc aggattaatg tacttaattc agctttttcc actacaccac acagcctcct | 420 |
| gtaaaacacc ctccctgcac acaacttacc cccaaagcac caggaaccta gctggctaga | 480 |
| gttgagctta ggaaaaacct gagtggctcc agagtcaaac tgcgataacg ttgagtcaga | 540 |
| ggagttaagg acaaagtaga gctgcacaga ggcccacgtc gtgcaagtgc gtgtctcctt | 600 |
| cagagaaagg cgtgccgagg tagactaggc cccgggcagc aaaaaccctg tcccgtcgcc | 660 |
| agcgcccgca ccgccagagc gactggagca gacgcgagcg ctgggcacgt agccggtggc | 720 |
| gcgcacgctc agcccgaggc cgcacgggag gctgtctggc gtgcgcgccc ccgcggcggt | 780 |
| gggcggggtc cggggcgggg ccgcaggagc agtaggtgtt agcagcttgg tcgcgacagg | 840 |

<210> SEQ ID NO 4
<211> LENGTH: 1200
<212> TYPE: DNA
<213> ORGANISM: Homo sapiens
<220> FEATURE:
<221> NAME/KEY: misc_feature
<223> OTHER INFORMATION: FAT10 promoter NCBI acc. number AL031983

<400> SEQUENCE: 4

| | |
|---|---|
| agtagaaacc tacttcaagt tcccataaaa tcatctgctt ttcactttca gtacagtatt | 60 |
| aatactta aatgagatat ttcacacttc agtagtaaat cacttttttg ttagataatt | 120 |
| ttgtccaact gtatgctaat gtaagtgttc tgagcatgtt taaggcaggt taggttaagc | 180 |

-continued

```
tatgatgttt ggtgggttag gtgtattaaa tgcatttctg attttggata ttttcagtgt    240
acaatgggtt tacagggatg taaccccatc ataagtgaag gagcacctgt acttacttca    300
ttaaaatgct gaaacagtaa ataaggtaac atttaataat atgttgtgca gttcttgaaa    360
tttaagtact caccaaatat tacttttcct ttttttgtta tttacttact tttcattcat    420
ttattaattc atttgtgcat ttagtaaaca tttataaatt atttcctgtg cctgacagca    480
tgctggaaca gtgctaaaga tacaagttaa ttaagacaca atcacgaccc ccaagattcc    540
tactcttttc taaagattac agacaagcag acgatgctat tgttgaagaa acatgctctg    600
agaggcattt gaaggaagtg tagaggatag aagatggaca cataacccag gatggggagg    660
aaaagagtta gggaaggctt tttgacgaag atactgttta caccgtgtgt tcttataaat    720
tcatggtggt ggggatagag ttggaggaaa aggcatgctc agtggcgtgg agatggcaga    780
gagattgggg tgttcaagga tatgccggga attcaaggaa cgagaattcc catagacaca    840
gacacagcta gacatagaga tctgcagctt aggtttgggc tgtgggtata gatccaggtg    900
gcttcaacag acaaagatct ttcctgagaa aagggaaaag ttttcaacac agaaagacca    960
tcccatgttt ggaatgaggt ttgcaaatag attgcttgag gagagaagta tgtgatcaga   1020
aagcattctt tgtctattaa ctcctgccca gcaaaagtga aagaaaattc atgggagcat   1080
gcaagaacaa agagcacagc aaagctggac aaacacagca atccaggcag gggatttcca   1140
actcaactct ggtatataag ctgcatgcaa agtccttttt ctgtctctgg tttctggccc   1200
```

<210> SEQ ID NO 5
<211> LENGTH: 1478
<212> TYPE: DNA
<213> ORGANISM: Homo sapiens
<220> FEATURE:
<221> NAME/KEY: misc_feature
<223> OTHER INFORMATION: PA 28 alpha promoter NCBI acc. number AL136295.2

<400> SEQUENCE: 5

```
gtggagtggg caccgcgaag ggaaagcgaa agcggtaggg cgctcgcacc cagctccgcc     60
ttcctgggta gtgggcgggg gagggctgga ggaggcgggg tcggatggag gaggcggggt    120
cagccctgcc atggaagggg cggtgccgca gaggagggcg gcgggtgagg ctccgcctag    180
cgcgcacagg cgctcttcac ccaccctccc cgcgccgcct cgcgagggcc agcttccagg    240
ctccccacct ccgctggccc ggtccccgcc tcccgcctcc cgccacctgc cgcccgccgc    300
ctgaggacgg cgggtccggg tcctcccatc gccaagccca agccagtctc tccgcgtccc    360
aacctccacc tccgcctcc caactggctc ccacctgct ctcttcttcc cctgctccgc      420
ctgggacaga taagctttac ttagggctct tccgtctttc cctagagatg gaataagacc    480
tggcctgtct ttcctagcct tgctagcgtg ggcctctggc tctgccgaca tcctgcgcac    540
ctgtagcaac ggcaccagag ctggcagcat ccctatccaa gcccggacca actctctcct    600
ggaccacggc tgcagatgcc attctataac ccactctcac ggagcagcgg gttcatgcct    660
ctctctggct taaacccctt tctcagctgc ctgttgacct ttgaatgaaa tccaaaagct    720
gtcgcacctg tctccccttt aagtccactt tctactgctt gccccttcat tcattacact    780
tgcaaatatt tgggctattt gtttctcaga tgtgtcatgt tcatttctgc ctcagggcct    840
ttgcccttgc taataatccc tttgcctaaa acacccttac cctgggtgtt gtcattggtt    900
ctcagtttag atgtcacctc ttcagagaga actatttca tcatccttta taaggaacct     960
```

-continued

```
ccctccaaat ctattacaaa tcatcctgtt ttagtacatt catagcattt atctctctga    1020
tattagccag gtgttttttt ttttttttcc aggataattt actgatttaa accaggtttt    1080
ggcaaacgtg tgtgtgtgtg tgtgtgtgtg tgtgtgtgtt gggggacgga gtctcgctct    1140
gtcgcccagg gtggagtgca gtggcaccat ctaggctcac tgcaacctcc acctccaggg    1200
ttcaagcgat tctcctgctt cagcctacgg agtagctagg actacaggcg cgtcccacca    1260
cgcccggcta attttttgta ttttttagtag agacgggggtt tcaccatgtt agccaggatg    1320
gactcgatct cctgacctcg tgatccgccc gcctcggcct cccaaagtgc tgggattgca    1380
ggcatgagcc accgcgtctg gccaactttt tctataaagg gccagagagt aaatatttta    1440
ggctttatag gccttacagt gtctgtctac tcaactct                            1478
```

<210> SEQ ID NO 6
<211> LENGTH: 3271
<212> TYPE: DNA
<213> ORGANISM: Homo sapiens
<220> FEATURE:
<221> NAME/KEY: misc_feature
<223> OTHER INFORMATION: Mac-2 BP promoter NCBI acc. number U91729.1

<400> SEQUENCE: 6

```
aagcctcccg aatagctggg attaaaggcg cctaccacca tgtttggcta attatttgta      60 ttttttgta gacacggggt ttcaccatct tgaccaggct ggtcttgaac tcctgacctc     120
gtgatctacc cacctcagcc tcctgaagtg ctgggtagtt tcttaaaaag gtaaacatat     180
atctaccata tgacccagta atcctgctcc taggtattta cacaaaataa atacttattt     240
tcacacaaag acttgtatcc aaatgttttcc agcagcttta tgcataatag tggaagatgg     300
aatgacccaa atgtccatca gtgcaaacat gtattaacag tggtgttctg tccatacagt     360
gggccgccac ccagcaaacc caggagccag ttactgattg ttgagatagc atggatggat     420
ctcagaagca ctgtggtaag taaaagaagc acatgcaaa atattaaata ctgtatgatt     480
ccatttagag ggaattctag ggtccaggag tggtgcctca tgcctgtaat cccagcactt     540
tgggaggcag aggcagggcg ggatcacctg agttcagggg ttcgaggcca gcctggccaa     600
tgtggagaaa ccccttctct actaaaaata caaaaattag ctggccgtgg tggtgggcgc     660
acctgtaatc ccagctactc gggaggctga ggcaggagaa tcacttggac ctgagaggca     720
gagattgcag tgagccgaga ttgttccact gcactccagc ctgggcaatg gagggagact     780
gtgtcttaaa aagaagaca aaatagaggg aattctagga aaggcaacca gcagtggcag     840
aagctgagag gtggttgctg ggaagggggct gggggaggtg gtggctgcag agggggbataa     900 gagaattctt aggggtgatt gaaacgcccct aggtaatgat tgttgtcatg ataccatcgc     960
tacacatttg ccaaaacttt gcacgtaaat tatatgccaa gaaagccaat ttttaaaaag    1020
aaggaaagga tgggtttgaa acccccagttc ttccccctacc agctgcacaa ctttagccga    1080
ttacgtcgcc tcactgagcc tctgtttctc catctgtaac agggaatata agagcagctg    1140
cttcccatca tggctggaag tattaaatgc attcatttgt ggcaaggctt atagtaatgc    1200
ctggcgaaat ccatattagc tattataggg agcgttcctc aatttgcgga gaggtttggg    1260
gtagaggcac aaaagatgac cttacaggcc agttaaccat tctcatctct gaaatgcccc    1320
gcactttccc ttccatgtct tgggagcggc ttcctgatga cagcagttct gtccacacga    1380
atctgaggct ttcacccagc tgtcttctca gagccgagcc gctgccctt ccctgcctg    1440 tcccctgtca gcgcttccct ccaccccatg gtcatcgcac accggaaagg ccttgcgagc    1500
```

-continued

```
cccaggggag cagatgktyg gtgctccgat tccacgagga ggcctctggg ttttccattt      1560
tacctgcctg gatggcttag gactttcccg gactctgggc taaagattcc ggcacctgag      1620
ttttaaaacc tttcccagca cttcccagag atgccctccc gtcctctgca ctcctgtcct      1680
tccctggcca cttgggcaga agtcattagc actgctgaga agggatgatg ctggggtttc      1740
tgtgcactca ggcccttaat ccggatgaga tttttttaaa ctccccacag ccagttctat      1800
ttccagctgc acctgcccct ggatcttcac aagttcctct ggagggggatt aggcaaaccg      1860 tgcagctgcc taaaacctca caccttgaag gaaatagtca ttgaatgtct gacctctggg      1920
ctggctgtct cggactctaa gctgccaggg aaccagggcc ttccacccag tgggactgcc      1980
tgggggcttt taaatgcccc tgcctgtccc ctactcccag agatggtgac ttcctgggtc      2040
taggcattag gagtttgtaa aactccctga tgattccttc tgtccagccc aggctgagaa      2100
ccactggtca gaggcctggg cacatcccaa ggctcatcca gaaccatggg gtgcaagtga      2160
cagaaacaag agcggctgct gattgcctca ctgagcagtg aagcccagcc ttgaccatgg      2220
attaggccag ctggacccag gagctcaggc cggaggatgc ctgcttccct ctgctctgcc      2280
ccaccggccc cagcagcctg ggcccacatc tctcagtca gaagctggct ctcaccggct      2340
ggctgggctc acagccccac cctgaaacca gcagtgtggc ccggggcccc cgcaggctca      2400
gacagccagg ccttgggtgg ttgaaggcca agagctgggg gccctctggg aaccacacag      2460
ccgggaatgg gagggggtgc tccccaaggg acagttgagg tgccggcttt cagtgggagg      2520
aaagggaatg ggtatgagct ggacagagcc attatgtcac ccagagaggc tctgtccccc      2580
gccccgctga gggggagaca gtaggagagt ggccacaggt ccagcagtgg cgagcacagg      2640
ctctggggtc aggtgttgga gcagggtcca gctcctccac tggccagctg catacctggt      2700
tctcagtgcc tccctcccct ggggacaggg gacagtgcca tgcaaccttg tggggcacag      2760
gccctctgtg tggtcagcat gccaagagca cagagagggt ggatttgcac atgagcagcc      2820
ccctgtgtgg tgttcaccca gccagcaacg tgctagaccc aggaaaagac tcggagcgct      2880
ctgtcagagt ccacagccac accaccaggt gcagactgtc tgggcccaga gcctctgctt      2940
cttcccctcc cgtccaccaa acgccagccc ctgaccacct ggcggccttt ccaactgagt      3000
gtggctgtta gtcctcttgc aggccttgct ccagccagac tcccacctgt ggcctctgcc      3060
agcctggcac tgatagccac aggcagagct gagacaaaag agaggggccc tggggagtat      3120
cagcagcagc caatcccgga agacatctat gtcaggtggt ttctggaaat cgaaagtaga      3180
ctcttttctg aagcatttcc tgggatcagc ctgaccacgt ccatactgg gagaggcttc      3240 tgggtcaaag gaccagtctg cagagggatc c                                   3271
```

<210> SEQ ID NO 7
<211> LENGTH: 1500
<212> TYPE: DNA
<213> ORGANISM: Homo sapiens
<220> FEATURE:
<221> NAME/KEY: misc_feature
<223> OTHER INFORMATION: PCI promoter NCBI acc. number AL049839.3

<400> SEQUENCE: 7

```
ctgccatgcc tactgctcac acttccatag cacgtgcccc caagcacccc atggtgtagg        60
tgctgttatt atcactatct tacagttatg gagcagtggc tcaaggtgta actgacttgc       120
ccaaaatcac actacaagga cacagcaggg ctgagatttg aacccaggca gtggcttcag       180
agcctgagct gtttcctact gcagagggag gaggcaagac ttctacccgt agccagatgg       240
```

-continued

| | | | | |
|---|---|---|---|---|
| ggaggcatgg | gcacaggaac | ggctcttggg | tgaagtggag | ggaggaagag gaggactgaa | 300 |
| ggccaaggcc | acgtcaggag | tgatgggaga | ccccacaaag | gcctcctga gaagagctag | 360 |
| agacaaagat | gagtgcctcc | tcatctggaa | gatgaaaaga | tgtctttgcc tgcatgggct | 420 |
| gctgtcacaa | agtcccaggg | gctaggggc | ttcaacaaca | gaaatttctt tctttacaac | 480 |
| tctggaagct | ggaagtctga | gattaaggca | ccagcaggat | ttgttccttc caaggcccct | 540 |
| ctccttggct | cacaggtggc | tgccttctcc | ctgtcttcac | ctggtcttcc ctctgtgcat | 600 |
| gtctctatcc | tgatctcctc | tttttaattt | ttgtgtaagg | acgtagtcat attgggttgg | 660 |
| ggcccactct | agtgacctca | ttctaactca | gtcccctctt | taaaagccct atctccagat | 720 |
| atagtcacat | tctggggtat | tgaaggtaag | gacttcagca | tatgcatttt ggggcacaa | 780 |
| ttcagccaga | acaggaggac | ggtggggatg | tccacatgaa | gaggttcagg cagaattcct | 840 |
| ttaggagggg | aagatgtctc | tctgtgggac | aagggtggca | tggagcagcc cctgggggaa | 900 |
| ggagaagggg | acagtttgca | tactggtatt | ctgcctaccc | caggtggac actcactcag | 960 |
| cgtttgctga | atgaacaggg | caaggccagc | agtgctgatg | gtcccaggca tgtagctggt | 1020 |
| ctgagttcat | agaaggacca | cagcgccctg | ccatgtgcca | aaccaggaca ccagagtgaa | 1080 |
| ggccagaagc | tcacatggaa | gcagcttagt | tccctggtaa | cctcgagatg ctgatgagac | 1140 |
| agagcagagc | agagggaacc | ctctccctcc | atatcccatc | ctccaaaatg tgtcccttga | 1200 |
| tgtggatggg | tagacaggat | tcctgccctg | gcagccagac | ccctgccttg ggtctgcacc | 1260 |
| tcctctccct | ccttcctctc | ccgtcatcc | ctaaatcttg | tcctcgagcc actgccaccc | 1320 |
| tgtgtaaacc | ctcatgccca | gtcttgcggg | tgccatccct | tctctttgaa gctgaatgga | 1380 |
| ccaaacatac | ccattgagtg | ttgggtgggg | acatctctgg | aaagtcagca cctggaccag | 1440 |
| ctccacccct | ctctgaggac | accttctttc | cctttcagaa | caaagaacag ccaccatgca | 1500 |

<210> SEQ ID NO 8
<211> LENGTH: 1674
<212> TYPE: DNA
<213> ORGANISM: Homo sapiens
<220> FEATURE:
<221> NAME/KEY: misc_feature
<223> OTHER INFORMATION: T cell receptor gamma promoter NCBI acc.
      number AC006033.2

<400> SEQUENCE: 8

| | | | | |
|---|---|---|---|---|
| cttacgagcc | ccaaggactg | ccagcgttga | tgtgtggagc | agtgacagca tgtctgcagg | 60 |
| cactgtgctt | tctgccaggg | cagcctgaaa | tcaccgcaga | gaagcgttag acctctgtgg | 120 |
| cttggctgag | tccaccaagt | caaacttccc | atgggtgagg | gtgacatggg gccccctgca | 180 |
| tcgttgtaaa | gcggtgtcct | caccacctgt | tagcacttcc | agtctgtgtg aagacagtcc | 240 |
| tgcaaggtct | gcagcctgag | atcagaccac | atagtttaga | cggccacctc agaccacaag | 300 |
| gcggccaccc | cagcaagttg | tcaggctggt | gttgttggtt | gctggggctg tgacatgcag | 360 |
| cattgtcttc | tgagagcttg | tcttcaacca | gctggagaga | tgttggtccg tcaagccgct | 420 |
| tagctctgct | cagctacccca | cacagcctgc | agcaccgggt | ccttctggtc accttctgatga | 480 |
| ggctgggccc | tccatcccag | tttgtttgct | tctgttgaag | attcaggttc ctgtcccctc | 540 |
| cctcagctac | ctgaataatg | tacatctcct | gaatcccggc | ttctcctcaa tgacagtttc | 600 |
| ctattgtctg | ttgttcttc | tctaagccaa | gacatttaat | ccgtcccaag gtatttttac | 660 |
| aaactgctct | ccccagtgca | tccctttaaaa | gctgctgtgt | tccagatttc catgcttaat | 720 |
| ttacccactg | ggagctgcag | ctcactgcca | ctgcccagca | tcgcaagaga gtatcataac | 780 |

```
cttatatcac tgtcctgggg aaacagcaaa ggtcaaatta tgttttctac caaatgcgtg      840
tcacttttgc accatcataa agtaaaaaaa aatcttaagt cggacctcag ttaaatcgaa      900
agctgtctgt acccatatcc agctaactct tggacatttt caagtacgtc tgacatggga      960
tctcaaacaa agtctgctca tagccagagt gaactcattc ccttccccca aaccatatct     1020
tcttccgagt tccctgtatg cataactacc cacattgccc aagccaggag cttgagcatc     1080
agcctcaatt ctccctcta attcaccgca ctctaattcc tgaggattct acgtcctaaa      1140
catttcctgg ctcaccactg cctccacctc acgcacctcc atacatccca tctcggcccc     1200
tcccacccac cttccccatg ccactagac tgacctggtc cttttcctgc tctaaagtcc      1260
ttgctctctc taccttgcct ctgaagatga agtccagagt tcttaggata agaggttctc     1320
tgtgatgtgg ccaccccctc cctgtccttc catcttcatt tagtcacttt ctgcctggaa     1380
ttccacgacc cacttctatg gattgacttg aattttttg tgtttggact gcattctact      1440
ccacattccc tggctaattc ctgtttatcc ttctgggctc agcccaggc agtcttcccc       1500 aggaagctta cctcacccag taagtccagg atggagatgc ttcaaattgc tttctcttca     1560
cgccacctag tgccttcctc tctcctagca cctcctaccc aagtcttggc ctgtttaccc     1620
atttctctct cattctaaac gacagttaag agttcccagg ggagtaagat catg           1674
```

<210> SEQ ID NO 9
<211> LENGTH: 1510
<212> TYPE: DNA
<213> ORGANISM: Homo sapiens
<220> FEATURE:
<221> NAME/KEY: misc_feature
<223> OTHER INFORMATION: Retinal oxidase promoter NCBI acc. number
      AF010260

<400> SEQUENCE: 9

```
cacctatgaa gtgttcttgc cctctccccc ccaaaaattg aacctgaatt taatcaaagc       60
tttagatctt aatatttagt gcatagggaa ataagtagag tagaaaaaca ataccaggga      120
gaagcaatta gccacattca aaaatggtt catttcaata gaacaactga cctggttttct     180 ttttcaatgt gttaatagtg ttaaaaagtc tgttttagat gaaaagagac tgatgagacc     240
acatgcaaat acattgcaca gctttgtttg attcaaagaa gtcaagtgta aaagacatt      300 tttagacacg tgaaatggtg ttgcggctga ctaaaaggat gtgtatgtgt gttttttgaag    360 tatttagggc taaaatatgt ccaggattgg cttttaaata ctacaaaaaa tggagtatgc     420
caaaacgttg accattgtta aagctcagtg aagggcaggt agatgccaat tgcactcttc     480
acttttatgt gcaaagtttg gaaaattttca caataaaatt tttgtgttta cataaatgaa    540
ataacatggg aaaatgttct aaggtatggc aagtgaaaag aagcctggaa ataactagt     600 ttgtcccact taagttttta aaggtgttaa agtacatgt tcaaaaagt aaggatagac       660 taaaagtgaa cgtggtaagt tctaagttgt gggcttacag gtgttctta tttttatgct     720 ttgctgtatt ttccaagttt tttttttaag ttttccaaga tgttttacat ctctgttctt    780
atttaccaga taaactttgt ggttagttac tggataaact gtaaatagtg ataaaatttt    840
taagtttata tcaagatagc acttcatttt aaaaccagta attattaggt tggtgcaaaa    900
ttaattgcag ttgttgccat tggaagtgat ggtaaaaacc gcaattactt ttgcaccaac    960
cttatatttc taaagatca agttgtaaac ctatttgttt tccctaagat ccgctcttgc     1020
agagttccaa taaaatgat tgtttacact taagagtcca ggactacagc aggcctggtt     1080
```

```
ggagggggagt tactaatgtt cccagactta aatccagctg gaacaccacc taaaatatgc    1140
agtaacataa gaccatcaaa agcaatgtcc caggacttac aatgtttgct aagacgcaag    1200
agggtgtgac acagacgcta agcgccactg gcgaggagat gaagggtcg tcttcatctt     1260 cgccggatga tttccgccca catagagggc gccagtgacg cccacacacg tgctggtgtc    1320
ccgggaagag ttcctggcaa agagctcagg taacgttgga tcttaattca aggctttctc    1380
cgttcggggt ggatgggttg gtactttagg ctccagcaag ccccgcccca ctcggcgggt    1440
cggtgccgcc gggtcccagg tgcccgctac ttcccagaac ctccgcctcc cgctccgggc    1500
cctcgaacca                                                          1510

<210> SEQ ID NO 10
<211> LENGTH: 1954
<212> TYPE: DNA
<213> ORGANISM: Homo sapiens
<220> FEATURE:
<221> NAME/KEY: misc_feature
<223> OTHER INFORMATION: Bene promoter NCBI acc. number AP001234.3

<400> SEQUENCE: 10
caaatatctg aagataaaa gcataaaaga aggagcttca ttagccagta tagagcatgt       60
ttccctttgc agggcatctc ttttctgtct ctagttaaaa gctcaggtga agttaggagg    120
gaaccaaggg ggaaatggag caggaagcct ggcccctctg agtcatggta aagtcacatc    180
cgattgttag gaaattcaag gggttgaaaa gcatgggcaa ggacttcatg tctaaaacac    240
caaaagcatc agcaacaaaa gccaaaattg agaaatggga tctaattaaa ctaaagagct    300
tctgcacagc aaaagaaaca accatcagag tgaacaggca acctacagaa tgggagaaaa    360
tttttgcaat ctacccatct gacaaagggc taatatccag aatctacaaa gaacttaaac    420
aaatttacaa gaaaaaaatc aaacaacccc atcaaaagt gggtgaagga tatgaacaga    480
cacttctcaa aagatgacat ttatgcagcc aacagacaca tgaaaaaatg ctcatcatca    540
ctggccatca gagaaatgca aatcaaaacc ataatgagat accatctcac accagttaga    600
atggtgatca ttaaaaagtc aggaaacaac aggtgctgga gaggatgtgg agaaatagga    660 acactttttac actgttggtg ggactgtaaa ctagttcaac cattgtgaaa gacagtgtgg    720
cgattcctca aggattgaga actagaaata ccatttgacc cagccatccc gttactgggg    780
atatacccaa aggattataa atcatgctgc tataaagaca catgcacacg tatgtttatt    840
gttgcactat tcacaatagc aaagacttgg aaccaaccca aatgtccaac aatgatagac    900
tggattaaga aaatgtggca catatacacc gtggaatact atgcagccat aaaaaatgat    960
gagttcacgt cctttgtagg gacatggatg aaactgaaa ccatcattct gagcaaacta   1020
ttgcaaggac agaaaaccaa acactgcatg ttctgactca tagatgggaa ttgaacaatg   1080
agaacacttg gacacagtgt ggggaacacc acacaccagg cctgttgtg gggtagggg    1140 agggggagg gatagcatta ggagatatac ctaatgtaaa tgaggagtta atgggtgcag   1200
cacaccaaca tggcacatgt atacacatga aacaaacctg cactttgtgc acatgtatcc   1260
tagaacttaa agtataataa aaaaataaaa taaaataaat aaaaaataaa aaagaaatt    1320 caagggttta atgcagaaat cgtgaacaga gggactctcg accaactctg gcctgtgaat   1380
atgtcttgtt ggctcaagca gtattggcat atacactttt aaacaattct gaataagttg   1440
ccaacattta aaacaggata tttcacatgg aaaatccata aattcggtta tattgcttag   1500
tatatacgtc tttggcacgc gattgaaacg cgctaattgc atcagcctat ctttctatgc   1560
```

| aagaatgcaa gaaaaattga tgtgatgtgc cttatcacaa ttcattacct cctatttcct | 1620 |
| ctgcagcaac aagtttcctt gattataaag gtctttagcg tgagaggtac aggtgttatg | 1680 |
| gcacgtgcga ataagggcag aaattaatca aatttatcaa ctatttggcg atggctcgag | 1740 |
| acaggtatag aaccactact aggtgatatt gaggcttttg tacaatttat agcaagtttt | 1800 |
| tgagagtccc ttcaagtttg ttacataatc ttctttgtgc aacgtacaag agcaaagtag | 1860 |
| aaaaatttgg tttttatttt tttaagcaac atcagctgca ctagttgagc ttttgacaag | 1920 |
| acatactgct caaaaaatct tcataacatt attt | 1954 |

<210> SEQ ID NO 11
<211> LENGTH: 1520
<212> TYPE: DNA
<213> ORGANISM: Homo sapiens
<220> FEATURE:
<221> NAME/KEY: misc_feature
<223> OTHER INFORMATION: HIF-2alpha/ EPAS promoter NCBI acc. number NT_005065.3

<400> SEQUENCE: 11

| caacttcaag ttacacctgt gaaactcatg ggtccttcca cagccttcaa aaactaaggg | 60 |
| cgtcccctgt cctctcccca gatgtccctt ccccatcgcc ggtagcgagt gggagacagc | 120 |
| tcagcgcggg gcaggggagc actgggcccg gagatggaag gcagcgtcaa aagcgccgct | 180 |
| ggaaaatccc tgagcgctaa ccgttgcctg tgtgagccct taaatctaca aatttccaac | 240 |
| acctgtagcc tttgggtttc ccaggacttc catcgaccct gcggcagag agggcaggcc | 300 |
| tgagatgcag tgacttgagg gcacatggcc aactcttgtc actccaagat cacactgggg | 360 |
| aaccagactg acttctccaa ttctgaactc gccccggcct cgggcggctc aaagggcctc | 420 |
| ctctgccgca tccccgccaa aaccaaaccg cctggcacaa gccggtaagc aaccaccctg | 480 |
| ctgggagagg gaaggaagag taggcgcagc cctagatcaa tttccttgca ctgcttctcc | 540 |
| cagacggtca agtcagctgc gtcccaccga aaagggcgca tcgcccacgc ccgaaacgca | 600 |
| gccgctgggg gccgagaaat tatccccacc tggcccgagg gccagggacg caggagcgca | 660 |
| gcagcgtgga ggggctccgc gctggcccgg cgctgcccgc ggtcctgccc tcgttccaag | 720 |
| ggcacgcgc cggtacgagg acaccgacgc tgtggcgcaa ctgccgtccc ccgcagcaat | 780 |
| cccggagccc ggctcccggc cgcccctcgg ccctgcgcag gctgcctctc cccgacgcgg | 840 |
| agtcccaccc cgctacccgc cgcccagacg acctcataaa caagtcctcg aagtgcggag | 900 |
| gcaggaggcg gggcgcagcg cggggggcagg aggcgggcca gggtcagggc agaggctgcg | 960 |
| gccgcgcgtc cccattggcc gggacgcagt gagccgcccg gagctcggcg cgggcggggc | 1020 |
| ctgccggcgc gtgcccgccc acacacccgc gccggtgccc gccccccgcc ctccgcgccc | 1080 |
| gccccgtgcc cgcccaagc cggccgacgg agtttttaaa gtgggctgcc ggccgcggga | 1140 |
| gctttacact cgcgagcgga ccgccacacg ggtccggtgc ccgctgcgct tccgccccag | 1200 |
| cgctcctgag gcggccgtac aatcctcggc agtgtcctga gactgtatgg tcagctcagc | 1260 |
| ccggcctccg actccttccg actcccagca ttcgagccaa tttttttttt ctttgaaaac | 1320 |
| tcagaaaagt gactcctttt ccagggaaaa aggaacttgg gttcccttct ctccgtcctc | 1380 |
| ttttcgggtc tgacagcctc cacccactcc ttccccggac cccgcctccg cgcgcaggtt | 1440 |
| cctcccagtc acctttctcc accccccgccc ccgcacctag cccgccgcgc gccaccttcc | 1500 |
| acctgactgc gcggggcgct | 1520 |

<210> SEQ ID NO 12
<211> LENGTH: 1469
<212> TYPE: DNA
<213> ORGANISM: Homo sapiens
<220> FEATURE:
<221> NAME/KEY: misc_feature
<223> OTHER INFORMATION: Selectin promoter NCBI acc. number AL021940.1

<400> SEQUENCE: 12

```
catggctttg cttggtcctt ctctagttct tctgcagccc attgagcctc ttgacttagc      60
acaagggtct caggtccttg cccaaaggga gtgtgctgtg ctgcaggtag actgcactga     120
atgtcaacag aaagccttgc tttctttcat tctctaacc cagtctcaca tcctcctcct      180
cctcccttt tcctcccct tcctcctgca cttctctttc ctctttcccc accccttcc       240
tagactggcc tctattgcct cccactgaga caaaaatgaa ctgctgatca aaagtaatgt     300
gactagattc tctcttcctt ccctccttc tatccttcct tccattctcc tatgcatctt     360
tccttaccct cctcctcctt cactcattgt tgttgctgtt cttcttcctc ttcttttcc     420
tcctgctcct cttcttctac ttgttcttgt tcttgttttt gtttggttct tgttctcctc    480
ttcctccttc tctctctcct cctcctcctt cttttccacc accctcccct atcttttca     540
taaatgctaa actaactctt ggctacctgt ggtaaatggc ccttggaaat tgcaaatact     600
acaaatcaaa actgcatttc agacatattt atgatgtttg caaaacttca gtagagctaa     660
gcagtggact tgactcgttt cggttccttc acctccgtct ttccttgctc accacctagt     720
ggacgtcctt gttagtggca cttcctgaag ttaaccccctg aagagagccc atgctctcta    780
gcttttcacc gtgtaggttt gggagcctac aagtaccttt aatattcttg gactataaaa     840
tgagatggtt ttataagact gcatgtgaaa ttaggaccca tatgatgaag gacaataaaa     900
aggaagaccc actgatgtga gtcaatgagt caaatgcaaa tcagatttgc attttagga     960
aaataataat aacaacaaca aaactctga agctcagcgc cccatattta ttatattgtt   1020
taatcttat aacagctctc tgctatagat atgattatta tccccattct aaagagtctc   1080
aaagaggtta agaaacaaat tcaaaaacta gcgaaagaca agaaataact aagatcagag   1140
cagaaccata ggaggtagag acacgaaaaa gccttcaaaa aatcaataaa tccaggagct   1200
gcattttgaa aagattaaca aaatagatgg accactagct agactaataa gaaagaagaa   1260
tcaatagaca caataaaaaa tggtaaaggg gatattacca ctgatcccgt agaaatacaa   1320
actaccatca gagattacta taaacatctt tacacaaata aactagaaaa tctagaagaa   1380
atggataaat tcctggacac atacaccctc ccaagactaa accaggaaga agtcaaatcc   1440
ctgaatagac taataacaag ttctgaaat                                     1469
```

<210> SEQ ID NO 13
<211> LENGTH: 1490
<212> TYPE: DNA
<213> ORGANISM: Homo sapiens
<220> FEATURE:
<221> NAME/KEY: misc_feature
<223> OTHER INFORMATION: Ring finger protein RNF promoter acc. number
    AP000518.1

<400> SEQUENCE: 13

```
taaatcatca tgccagtcaa acaaaacctg tcaaagtta aattctgctt ctaggggcca      60
gcagtttagg agtataagta aaacaattta cagatgttag actgttttaa tttaaccta     120
aaacaaacaa aaagaaaggt ctggaggtat aacattctg aaagtctttg gtttacagca     180
gttgctataa ggggagccac ataatttata gtccaaactg gacatttctg aaagtgaaag    240
```

-continued

```
gaggtgctat taataattac accaggacaa agtgaaaccc aggatggttc caggcaaagc      300
agagtgtatg atcactctgg ctattattat aataatcatc cacaagccct gtttgaccta      360
agattaagat cagacaaaaa ttaatggtgt acttcttgct ggggacagac ggctgataat      420
ggagagtgag gaggtgaggg tggaagctat accaagagaa ggggtaggga ggaagcaccc      480
ttttccttaa gacaagaggc aaggagggaa ggttaggaca tgaatgtaca gaagggaatg      540
tatgtaacac tggttgatat attcctagtc ataacaaaag ccatagaagg caagtcaggg      600
atcagagaag caccaagaag gaagaagaag aacatataga cagaattggc aaagcaaaga      660
atgggcacgg agacaccagc atactggaga catacagaga aaaaatcaac agaggacaga      720
ctactacagg tgttgtgggg aggcagaaga tcaccagggg caagagcaaa gtgcaaaaac      780
aaagaacaac tctttagaaa ggaagttcct tgcctatcct actgagctag agagtggttg      840
gttgaccctg tgactggaaa ttccccaagg taggtgatga taacctctac attttcacaa      900
aattctgtga ggagccaaag cacctgaggt agagaattgc ccttcccta ctttccagat       960 gctctaccaa ggcttgaact ttgcatacaa gatgcccaaa gcattgcagt gaactggctg     1020
tgacctttca gtaggcatca ccacccaccc ctccactccc tactcagagc tgattgggaa     1080
atcccccata agtggtgttt ggtgccccgg tcattctgat tttagtcaac caccatacaa     1140
acataccttt agtccaaagt tcaggacaac ttatttcact ttataagcag cctattacac     1200
attcaaagta tccatttgtt ctcaagaggt agcaaggtag gactgcccat ctgttttcct     1260
ctctttataa tattttctag atcctaaatt ttacgctttt ctatcattta ttttttttctc    1320 cctcttcttt tcctctctct ctgctcttct aactaattgg cagaatctct gacctccact     1380
ttctctgact cccttctccc ttcctagaaa cagtatccac agtggactcc ggggctccta     1440
cagacttggc acagcttcct acagtcttga aacagccctg ttgttctgtc                1490
```

<210> SEQ ID NO 14
<211> LENGTH: 20
<212> TYPE: DNA
<213> ORGANISM: Homo sapiens
<220> FEATURE:
<221> NAME/KEY: misc_feature
<223> OTHER INFORMATION: Sense primer for IGFBP-3

<400> SEQUENCE: 14
ttgcacaaaa gactgccaag                                                    20

<210> SEQ ID NO 15
<211> LENGTH: 20
<212> TYPE: DNA
<213> ORGANISM: Homo sapiens
<220> FEATURE:
<221> NAME/KEY: misc_feature
<223> OTHER INFORMATION: Antisense primer for IGFBP-3

<400> SEQUENCE: 15
catgaagtct gggtgctgtg                                                    20

<210> SEQ ID NO 16
<211> LENGTH: 20
<212> TYPE: DNA
<213> ORGANISM: Homo sapiens
<220> FEATURE:
<221> NAME/KEY: misc_feature
<223> OTHER INFORMATION: Sense primer for Mac-2 BP

<400> SEQUENCE: 16
aattccacac tgtgcccttc                                       20

<210> SEQ ID NO 17
<211> LENGTH: 20
<212> TYPE: DNA
<213> ORGANISM: Homo sapiens
<220> FEATURE:
<221> NAME/KEY: misc_feature
<223> OTHER INFORMATION: Antisense primer for Mac-2 BP

<400> SEQUENCE: 17
gtggagtctg gaaggactgg                                       20

<210> SEQ ID NO 18
<211> LENGTH: 20
<212> TYPE: DNA
<213> ORGANISM: Homo sapiens
<220> FEATURE:
<221> NAME/KEY: misc_feature
<223> OTHER INFORMATION: Sense primer for beta IG-H3

<400> SEQUENCE: 18
tgcgactagc ccctgtctat                                       20

<210> SEQ ID NO 19
<211> LENGTH: 20
<212> TYPE: DNA
<213> ORGANISM: Homo sapiens
<220> FEATURE:
<221> NAME/KEY: misc_feature
<223> OTHER INFORMATION: Antisense primer for beta IG-H3

<400> SEQUENCE: 19
catgcacaag gctcacatct                                       20

<210> SEQ ID NO 20
<211> LENGTH: 20
<212> TYPE: DNA
<213> ORGANISM: Homo sapiens
<220> FEATURE:
<221> NAME/KEY: misc_feature
<223> OTHER INFORMATION: Sense primer for PCI

<400> SEQUENCE: 20
gcacccaaga gcaagacttc                                       20

<210> SEQ ID NO 21
<211> LENGTH: 20
<212> TYPE: DNA
<213> ORGANISM: Homo sapiens
<220> FEATURE:
<221> NAME/KEY: misc_feature
<223> OTHER INFORMATION: Antisense primer for PCI

<400> SEQUENCE: 21
cgagctgcct cttttttgaac                                      20

<210> SEQ ID NO 22
<211> LENGTH: 20
<212> TYPE: DNA
<213> ORGANISM: Homo sapiens
<220> FEATURE:
<221> NAME/KEY: misc_feature
<223> OTHER INFORMATION: Sense primer for FAT 10

<400> SEQUENCE: 22
aatgcttcct gcctctgtgt                    20

<210> SEQ ID NO 23
<211> LENGTH: 20
<212> TYPE: DNA
<213> ORGANISM: Homo sapiens
<220> FEATURE:
<221> NAME/KEY: misc_feature
<223> OTHER INFORMATION: Antisense primer for FAT 10

<400> SEQUENCE: 23
atcactgggc ttcaccactt                    20

<210> SEQ ID NO 24
<211> LENGTH: 20
<212> TYPE: DNA
<213> ORGANISM: Homo sapiens
<220> FEATURE:
<221> NAME/KEY: misc_feature
<223> OTHER INFORMATION: Sense primer for EPLIN beta

<400> SEQUENCE: 24
agaaagggga ccctgactgt                    20

<210> SEQ ID NO 25
<211> LENGTH: 20
<212> TYPE: DNA
<213> ORGANISM: Homo sapiens
<220> FEATURE:
<221> NAME/KEY: misc_feature
<223> OTHER INFORMATION: Antisense primer for EPLIN beta

<400> SEQUENCE: 25
aagatcctca ccgtccttga                    20

<210> SEQ ID NO 26
<211> LENGTH: 20
<212> TYPE: DNA
<213> ORGANISM: Homo sapiens
<220> FEATURE:
<221> NAME/KEY: misc_feature
<223> OTHER INFORMATION: Sense primer for T cell receptor gamma

<400> SEQUENCE: 26
aggagctgtg gaaaacatgg                    20

<210> SEQ ID NO 27
<211> LENGTH: 20
<212> TYPE: DNA
<213> ORGANISM: Homo sapiens
<220> FEATURE:
<221> NAME/KEY: misc_feature
<223> OTHER INFORMATION: Antisense primer for T cell receptor gamma

<400> SEQUENCE: 27
cataacagac ggtggcacaa                    20

<210> SEQ ID NO 28
<211> LENGTH: 20
<212> TYPE: DNA
<213> ORGANISM: Homo sapiens
<220> FEATURE:
<221> NAME/KEY: misc_feature
<223> OTHER INFORMATION: Sense primer for P28 alpha

<400> SEQUENCE: 28
acaggtggat gtgtttcgtg                    20

```
<210> SEQ ID NO 29
<211> LENGTH: 20
<212> TYPE: DNA
<213> ORGANISM: Homo sapiens
<220> FEATURE:
<221> NAME/KEY: misc_feature
<223> OTHER INFORMATION: Antisense primer for P28 alpha

<400> SEQUENCE: 29
ttcatcctcc cccttcttct                                              20

<210> SEQ ID NO 30
<211> LENGTH: 20
<212> TYPE: DNA
<213> ORGANISM: Homo sapiens
<220> FEATURE:
<221> NAME/KEY: misc_feature
<223> OTHER INFORMATION: Sense primer for Retinal oxidase

<400> SEQUENCE: 30
gtggtggaca tcatgacagc                                              20

<210> SEQ ID NO 31
<211> LENGTH: 20
<212> TYPE: DNA
<213> ORGANISM: Homo sapiens
<220> FEATURE:
<221> NAME/KEY: misc_feature
<223> OTHER INFORMATION: Antisense primer for Retinal oxidase

<400> SEQUENCE: 31
agcggctcca agtcttgata                                              20

<210> SEQ ID NO 32
<211> LENGTH: 20
<212> TYPE: DNA
<213> ORGANISM: Homo sapiens
<220> FEATURE:
<221> NAME/KEY: misc_feature
<223> OTHER INFORMATION: Sense primer for Bene

<400> SEQUENCE: 32
ccaggcaaca aaaggagaga                                              20

<210> SEQ ID NO 33
<211> LENGTH: 20
<212> TYPE: DNA
<213> ORGANISM: Homo sapiens
<220> FEATURE:
<221> NAME/KEY: misc_feature
<223> OTHER INFORMATION: Antisense primer for Bene

<400> SEQUENCE: 33 tgcctttctgt cattgggaat                                             20

<210> SEQ ID NO 34
<211> LENGTH: 20
<212> TYPE: DNA
<213> ORGANISM: Homo sapiens
<220> FEATURE:
<221> NAME/KEY: misc_feature
<223> OTHER INFORMATION: Sense primer for HIF-2alpha/ EPAS-1

<400> SEQUENCE: 34
ccagtgcatc atgtgtgtca                                              20
```

<210> SEQ ID NO 35
<211> LENGTH: 20
<212> TYPE: DNA
<213> ORGANISM: Homo sapiens
<220> FEATURE:
<221> NAME/KEY: misc_feature
<223> OTHER INFORMATION: Antisense primer for HIF-2alpha/ EPAS-1

<400> SEQUENCE: 35
cccgaaatcc agagagatga                                           20

<210> SEQ ID NO 36
<211> LENGTH: 20
<212> TYPE: DNA
<213> ORGANISM: Homo sapiens
<220> FEATURE:
<221> NAME/KEY: misc_feature
<223> OTHER INFORMATION: Sense primer for Selectin

<400> SEQUENCE: 36
gtggcacctc ctacgtcaaa                                           20

<210> SEQ ID NO 37
<211> LENGTH: 22
<212> TYPE: DNA
<213> ORGANISM: Homo sapiens
<220> FEATURE:
<221> NAME/KEY: misc_feature
<223> OTHER INFORMATION: Antisense primer for Selectin

<400> SEQUENCE: 37
tgaatccttt ccctttatgg tc                                        22

<210> SEQ ID NO 38
<211> LENGTH: 20
<212> TYPE: DNA
<213> ORGANISM: Homo sapiens
<220> FEATURE:
<221> NAME/KEY: misc_feature
<223> OTHER INFORMATION: Sense primer for ring finger protein RNF

<400> SEQUENCE: 38
gaggtgcagt ccaaaaggaa                                           20

<210> SEQ ID NO 39
<211> LENGTH: 22
<212> TYPE: DNA
<213> ORGANISM: Homo sapiens
<220> FEATURE:
<221> NAME/KEY: misc_feature
<223> OTHER INFORMATION: Antisense primer for ring finger protein RNF

<400> SEQUENCE: 39
tgtgttggcg tacaggtctt tg                                        22

<210> SEQ ID NO 40
<211> LENGTH: 22
<212> TYPE: DNA
<213> ORGANISM: Homo sapiens
<220> FEATURE:
<221> NAME/KEY: misc_feature
<223> OTHER INFORMATION: Sense primer for Beta-actin

<400> SEQUENCE: 40
tgtgttggcg tacaggtctt tg                                        22

-continued

```
<210> SEQ ID NO 41
<211> LENGTH: 22
<212> TYPE: DNA
<213> ORGANISM: Homo sapiens
<220> FEATURE:
<221> NAME/KEY: misc_feature
<223> OTHER INFORMATION: Antisense primer for Beta-actin

<400> SEQUENCE: 41
tgtgttggcg tacaggtctt tg                                          22

<210> SEQ ID NO 42
<211> LENGTH: 17
<212> TYPE: DNA
<213> ORGANISM: Homo sapiens
<220> FEATURE:
<221> NAME/KEY: misc_feature
<223> OTHER INFORMATION: RARE sequence from ring finger protein RNF
      promoter

<400> SEQUENCE: 42
aggtcacagc cagttca                                                17

<210> SEQ ID NO 43
<211> LENGTH: 20
<212> TYPE: DNA
<213> ORGANISM: Homo sapiens
<220> FEATURE:
<221> NAME/KEY: misc_feature
<223> OTHER INFORMATION: Sense primer for beta-IG-H3 reporter gene
      construction

<400> SEQUENCE: 43
ggccaggtgc ctcttcttag                                             20

<210> SEQ ID NO 44
<211> LENGTH: 18
<212> TYPE: DNA
<213> ORGANISM: Homo sapiens
<220> FEATURE:
<221> NAME/KEY: misc_feature
<223> OTHER INFORMATION: Antisense primer for beta-IG-H3 reporter gene
      construction

<400> SEQUENCE: 44
cggctccagg gaagtgag                                               18
```

REAGENTS AND METHODS FOR IDENTIFYING AND MODULATING EXPRESSION OF GENES REGULATED BY RETINOIDS

This application claims priority to U.S. Provisional Application Serial No. 60/207,535, filed May 26, 2000.

This application was supported by a grant from the National Institutes of Health, No. RO1 CA62099. The government may have certain rights in this invention.

BACKGROUND OF THE INVENTION

1. Field of the Invention

This invention is related to changes in cellular gene expression and compounds that produce changes in cellular gene expression. In particular, the invention is related to the identification of genes the expression of which is modulated by a class of compounds known as retinoids, being chemically related to retinoic acid and Vitamin A, More specifically, the invention provides methods for identifying compounds other than retinoids that modulate expression of these cellular genes. The invention also provides reagents that are recombinant mammalian cells containing recombinant expression constructs that express a reporter gene under the transcriptional control of a promoter for a gene that is regulated by retinoids, and methods for using such cells for identifying compounds other than retinoids that modulate expression of these cellular genes.

2. Summary of the Related Art

Retinoids are naturally-occurring or synthetic derivatives of vitamin A. They comprise a class of clinically important differentiation agents that regulate cell growth and differentiation at the level of transcription, by binding to nuclear receptors that act as ligand-dependent transcription factors. These compounds induce cellular differentiation or terminal proliferation arrest in a number of tumor cell types in vivo and in vitro that express retinoid receptors (Warrell, 1997, in CANCER. PRINCIPLES & PRACTICE OF ONOCOLOGY (DeVita et al., eds.), pp. 483–490 (Lippincott-Raven, Philadelphia), making them useful for treating some cancers, such as acute promyelocytic leukemia and cancer chemoprevention.

The target of retinoid action is the cell nucleus, where retinoids bind to two types of receptors, termed RARs (retinoic acid receptors) and RXRs (retinoid X receptors) (Mangelsdorf et al., 1994, "The retinoid receptors," in: The Retinoids biology, chemistry, and medicine, Spain et al., eds., New York: Raven Press, pp. 319–351) Retinoid-bound receptor molecules form homo- (RXR—RXR) and heterodimers (RAR–RXR) that act as transcription factors. These dimers bind to specific cis-regulatory sequences in the promoters of retinoid-responsive target genes, termed RARE (Retinoic Acid Response Elements), regulating their transcription.

A RARE sequence has a minimal half-site consensus sequence that is generally well conserved as AGGTCA or AGTTCA (Mangelsdorf et al., 1994, "The retinoid receptors," in: The Retinoids: biology, chemistry, and medicine, Sporn et al., eds., New York: Raven Press, pp. 327–331). RAREs are typically configured into one of three structured motifs: direct repeats, palindromes, and complex elements without an obvious consensus structure. The direct repeat requires a lesser amount of receptor to activate a retinoid-inducible gene than the other configurations. In addition, direct repeats separated by 5 nucleotides have demonstrated the strongest responses while moderate responses are typically generated by direct repeats separated by 2 nucleotides. (See Mangelsdorf et al., 1994, "The retinoid receptors," in: The Retinoids: biology, chemistry, and medicine, Sporn et a!., eds., New York: Raven Press, pp. 327–331.)

The resulting changes in gene expression are caused either directly by retinoid receptor regulation of target gene expression, or indirectly through the action of retinoid-activated signal transduction pathways, for example, pathways activated by the transcription factor AP-1. These gene expression changes are ultimately responsible for the growth-inhibitory effect of retinoids (Warrell, Id.).

Although retinoids have had some clinical success in cancer treatment, their use has been limited by at least two factors: development of resistance (Miller et al., 1998, Cancer 83:1471–1482) or toxicity. Development of resistance is due in part to alterations of retinoic acid receptors and retinoid receptor-mediated pathways (Miller et al., ibid.). Toxicity is generally attributed to the broad physiologic consequences of retinoids, resulting from pleiotropic changes in gene expression produced by treatment with retinoids.

Several growth-inhibitory genes have been previously found to be inducible by retinoids in epithelial cells. None of these genes, however, was shown to be solely responsible for the growth-inhibitory effect of retinoids.

Adamo et al., 1992, Endocrinology 131: 1858–1866 disclosed induction of insulin-like growth factor binding protein 3 (IGFBP-3) in breast carcinoma cell lines.

Swisshelm et al., 1995, Proc. Natl. Acad. Sci. USA 92: 4472–4476 identified another insulin-like growth factor binding protein, IGFBP-7 (also known as insulin-like growth factor binding protein related protein 1, or IGFBP-rP1, and mac25) as a protein induced by treatment of cells with fenretinide (4-hydroxyphenylretinamide, 4-HPR). This protein was also shown to be down-regulated in mammary carcinoma cell lines.

Kato et al., 1996, Oncogene 12: 1361–1364 showed that introduction of mac25 cDNA into an osteosarcoma cell line inhibited growth.

Gucev et al., 1996, Cancer Res. 56: 1545–1550 identified IGFBP-3 as a protein induced in breast carcinoma cells both by all-trans retinoic acid (RA) and by transforming growth factor β (TGF-β). RA-mediated growth inhibition in these cells was alleviated by introducing an antisense oligonucleotide into the cells that inhibited IGFBP-3 expression, or by introducing exogenous IGFBP-3 into the cells.

DiSepio et al., 1998, Proc. Natl. Acad. Sci. USA 95: 14811–14815 showed that tazarotene-induced gene 3 (TIG-3, also known as retinoid-inducible gene 1, RIG-1), a putative tumor suppressor gene, is induced in primary human keratinocytes. TIG-3 shows decreased expression in cancer cells, inhibits the growth of cancer cells when expressed, and shares sequence homology with a known tumor suppressor gene, H-rev 107.

Huang et al., 2000, Molec. Cell. Endocrinol. 159: 15–24 showed that TIG-3 was induced by retinoids in a gastric carcinoma cell line in vitro.

Liu et al., 2000, J. Cancer Res. Clin. Oncol. 126: 85–90 reported that RA-induced expression of a metastasis suppressor gene, nm23-H1 in a hepatocarcinoma cell line.

The teachings of the prior art suggest that one mechanism of retinoid-mediated growth inhibition is the activation (or re-activation) of tumor suppressor genes and other growth-inhibitory genes that have been repressed or whose expression has been down-regulated in tumor cells. However, the reports in the art fail to indicate the identity or number of growth-inhibitory genes that are activated under the conditions of retinoid-induced growth arrest. Such reports also fail to indicate if retinoid-induced genes are induced by retinoids directly, through RARE sites in their promoters, or indirectly. In the latter case, it should be possible to activate such growth-inhibitory genes even in the cells that are not responsive to retinoids.

There remains a need in this art to identify genes whose expression is modulated by retinoids, and especially growth-inhibitory genes that are induced by retinoids indirectly. There is also a need in this art to develop methods for assessing the effects of compounds on expression of retinoid-modulated cellular genes, particularly growth-inhibitory genes. There is an additional need to develop alternative compounds that mimic the effects of retinoids on cellular gene expression, to which resistance is not so easily developed and that lack the toxicity and other systemic side-effects of retinoids in current clinical use.

SUMMARY OF THE INVENTION

This invention provides genes whose expression is modulated by retinoids and reagents and methods for identifying compounds that mimic the effects of retinoids without producing resistance or toxicity to said compounds.

In a first aspect, the invention provides a recombinant expression construct encoding a reporter gene operably linked to a promoter from a gene the expression of which is induced by a retinoid and which does not contain a RARE site. In preferred embodiments, the reporter gene encodes firefly luciferase, chloramphenicol acetyltransferase, beta-galactosidase, green fluorescent protein, or alkaline phosphatase. Preferred retinoids include all-trans retinoic acid, fenretinide, 9-cis retinoic acid, 13-cis retinoic acid, etretinate and retinol (Vitamin A). Most preferred promoters comprising the recombinant expression constructs of the invention are promoters from a cellular gene that is known to be induced by a retinoid and to have a growth-inhibitory activity. In preferred embodiments, the cellular gene promoter is from human insulin-like growth factor binding protein-3 (IGFBP-3; SEQ ID NO. 1), secreted cell adhesion protein βIG-H3 (SEQ ID NO. 2), epithelial protein lost in neoplasm (EPLIN; SEQ ID NO. 3), ubiquitin-like protein FAT10 (SEQ ID NO. 4), proteasome activator PA28 subunit α (PA28α; SEQ ID NO.:5), Mac-2 binding protein (Mac-2BP; SEQ ID NO.:6), Protein C inhibitor (PCI; SEQ ID NO.:7), T cell receptor gamma (SEQ ID NO.:8), retinal oxidase (SEQ ID NO.:9), Bene (SEQ ID NO.:10), HIF-2alpha/EPAS-1 (SEQ ID NO.:11), or selectin L (SEQ ID NO.:12). In particularly preferred embodiments, the promoter is from human insulin-like growth factor binding protein-3 (IGFBP-3; SEQ ID NO. 1), secreted cell adhesion protein βIG-H3 (SEQ ID NO. 2), epithelial protein lost in neoplasm (EPLIN; SEQ ID NO. 3), ubiquitin-like protein FAT10 (SEQ ID NO. 4), or proteasome activator PA28 subunit α (PA28α; SEQ ID NO. 5).

In a second embodiment, the invention provides a mammalian cell containing a recombinant expression construct of the invention encoding a reporter gene under the transcriptional control of a promoter from a retinoid-inducible cellular gene. In preferred embodiments, the reporter gene encodes firefly luciferase, chloramphenicol acetyltransferase, beta-galactosidase, green fluorescent protein, or alkaline phosphatase. Preferred retinoids include all-trans retinoic acid, fenretinide, 9-cis retinoic acid, 13-cis retinoic acid, etretinate and retinol. Most preferred promoters comprising the recombinant expression constructs of the invention are promoters from a cellular gene that is known to be induced by a retinoid and to have a growth-inhibitory activity or from human insulin-like growth factor binding protein-3 (IGFBP-3; SEQ ID NO. 1), secreted cell adhesion protein βIG-H3 (SEQ ID NO. 2), epithelial protein lost in neoplasm (EPLIN; SEQ ID NO. 3), ubiquitin-like protein FAT10 (SEQ ID NO. 4), proteasome activator PA28 subunit α (PA28α; SEQ ID NO.:5), Mac-2 binding protein (Mac-2 BP; SEQ ID NO.:6), Protein C inhibitor (PCI; SEQ ID NO.:7), T cell receptor gamma (SEQ ID NO.:8), retinal oxidase (SEQ ID NO.:9), Bene (SEQ ID NO.:10), HIF-2alpha/EPAS-1 (SEQ ID NO.:11), or selectin L (SEQ ID NO.:12). In particularly preferred embodiments, the promoter is from human insulin-like growth factor binding protein-3 (IGFBP-3; SEQ ID NO. 1), secreted cell adhesion protein βIG-H3 (SEQ ID NO. 2), epithelial protein lost in neoplasm (EPLIN; SEQ ID NO. 3), ubiquitin-like protein FAT10 (SEQ ID NO. 4), or proteasome activator PA28 subunit α (PA28α; SEQ ID NO. 5).

In a third embodiment, the invention provides a method for identifying a compound that induces expression of a retinoid-inducible gene in a mammalian cell. In this method, recombinant mammalian cells according to the invention containing a recombinant expression construct of the invention encoding a reporter gene under the transcriptional control of a promoter from a retinoid-inducible cellular gene are cultured under conditions that induce expression of at least one retinoid-induced gene in mammalian cells in the presence and absence of a compound. Reporter gene expression is compared in the cell in the presence of the compound with reporter gene expression in said cell in the absence of the compound. Compounds that induce retinoid-induced gene expression are identified if reporter gene expression is higher in the presence of the compound than in the absence of the compound. In preferred embodiments, the reporter gene encodes firefly luciferase, chloramphenicol acetyltransferase, beta-galactosidase, green fluorescent protein, or alkaline phosphatase. Preferred retinoids include all-trans retinoic acid, fenretinide, 9-cis retinoic acid, 13-cis retinoic acid, etretinate and retinol. Most preferred promoters comprising the recombinant expression constructs of the invention are promoters of a cellular gene that is known to be induced by a retinoid and to have a growth-inhibitory activity or from human insulin-like growth factor binding protein-3 (IGFBP-3; SEQ ID NO. 1), secreted cell adhesion protein βIG-H3 (SEQ ID NO. 2), epithelial protein lost in neoplasm (EPLIN; SEQ ID NO. 3), ubiquitin-like protein FAT10 (SEQ ID NO. 4), proteasome activator PA28 subunit α (PA28α; SEQ ID NO.: 5), Mac-2 binding protein (Mac-2 BP; SEQ ID NO.:6), Protein C inhibitor (PCI; SEQ ID NO.:7), T cell receptor gamma (SEQ ID NO.:8), retinal oxidase (SEQ ID NO.: 9), Bene (SEQ ID NO.:10), HIF-2alpha/EPAS-1 (SEQ ID NO.:11), or selectin L (SEQ ID NO.:12). In particularly preferred embodiments, the promoter is from human insulin-like growth factor binding protein-3 (IGFBP-3; SEQ ID NO. 1), secreted cell adhesion protein βIG-H3 (SEQ ID NO. 2), epithelial protein lost in neoplasm (EPLIN; SEQ ID NO. 3), ubiquitin-like protein FAT10 (SEQ ID NO. 4), or proteasome activator PA28 subunit α (PA28α; SEQ ID NO. 5). In preferred embodiments, expression of the reporter gene is detected using an immunological reagent, by hybridization to a complementary, detectably-labeled nucleic acid, or by detecting an activity of the reporter gene product.

In a fourth embodiment, the invention provides a method for identifying a compound that induces expression of a retinoid-inducible gene in a mammalian cell. In this aspect of the invention, mammalian cells are cultured in the presence and absence of the compound. The cells are then assayed for expression of at least one cellular gene whose expression is induced by a retinoid. Compounds that induce expression of a retinoid-inducible gene in a mammalian cell are identified if expression of the cellular genes of subpart (b) is higher in the presence of the compound than in the absence of the compound. Preferred retinoids include all-trans retinoic acid, fenretinide, 9-cis retinoic acid, 13-cis retinoic acid, etretinate and retinol. The gene is a cellular gene that is known to be induced by a retinoid and to have a growth-inhibitory activity or human insulin-like growth factor binding protein-3 (IGFBP-3; NCBI Accession No. M35878.1), secreted cell adhesion protein βIG-H3 (Accession No. AC004503.1), epithelial protein lost in neoplasm (EPLIN; Accession No. AH0093 82.1), ubiquitin-like protein FAT10 (Accession No. AL031983), Mac-2 binding protein (Mac-2 BP; Accession No. U91729), Protein C inhibitor (PCI; Accession No. AL049839.3), T cell receptor gamma (Accession No. AC006033.2), retinal oxidase (Accession No. AF010260), Bene (Accession No. AP001234.3), HIF-2alpha/EPAS-1 (Accession No. NT_005065.3), selectin L (Accession No. AL021940.1), or proteasome activator PA28 subunit α (PA28α; Accession No. AL 136295.2). In particularly preferred embodiments, the gene is human IGFBP-3, βIG-H3, EPLIN, FAT10 or PA28α. In preferred embodiments, expression of the cellular gene is detected using an immunological reagent, by hybridization to a complementary, detectably-labeled nucleic acid, or by detecting an activity of the gene product.

The invention also provides methods for treating an animal having cancer to prevent or ameliorate the disease. In this aspect, a therapeutically-effective dose of a compound identified by the invention that induces expression of a retinoid-induced gene is administered to an animal, most preferably a human, in need thereof.

Specific preferred embodiments of the present invention will become evident from the following more detailed description of certain preferred embodiments and the claims.

BRIEF DESCRIPTION OF THE DRAWINGS

FIG. 1A shows the effect of treatment with 100 nM RA for the indicated number of days. FIG. 1B shows the effect of 40 hr treatment with the indicated doses of RA.

FIG. 2A shows a time course of changes in gene expression on the indicated days after the addition of 100 nM RA. The designations "R5" and "R8" correspond to days 5 and 8 after release from 5-day RA treatment, respectively. FIG. 2B shows the effects of 40 hr treatment with the indicated doses of RA. FIG. 2C shows a time course of changes in gene expression on the indicated days after the addition of 1 μM fenretinide.

FIG. 3A shows the results of immunocytochemical analysis of IGFBP-3, HIF2α/EPAS-1 and EPLIN in untreated MCF-7 cells and in cells treated with 100 nM RA for 5 days. FIG. 3B shows immunoblotting analysis of EPLIN in untreated MCF-7 cells and in cells treated with 100 nM RA for the indicated number of days.

DETAILED DESCRIPTION OF THE PREFERRED EMBODIMENTS

Figure 1:
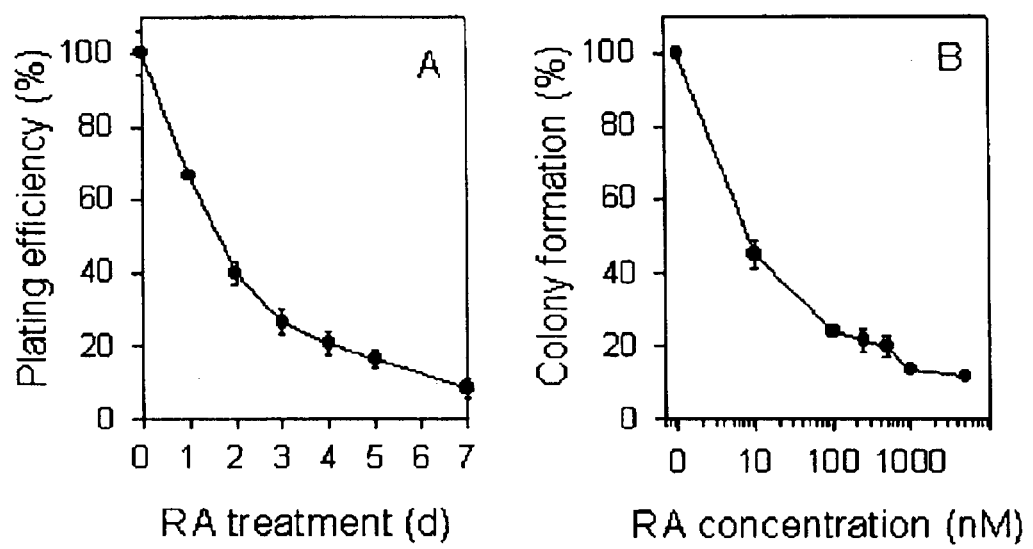
FIGS. 1A and 1B are graphs showing the effects of retinoic acid (RA) on colony formation by MCF-7 cells. In each assay, $1.5 \times 10^5$ cells were plated per P100, in the absence or in the presence of RA. For clonogenic assays, cells were trypsinized after treatment, and 2,500 cells were plated per P100 and grown in drug-free media. Colonies comprising at least 60–80 cells were scored 12–14 days after plating; these results were normalized by the number of colonies formed by untreated cells. Each point represents the mean and standard deviation for triplicate assays.

This invention provides genes induced to express by retinoids. The invention also provides reagents and methods for identifying compounds that mimic the gene expression inducing properties of retinoids but lack toxicity and propensity for cells to develop resistance that is characteristic of retinoid treatment.

The present inventors have determined that retinoid treatment of retinoid-sensitive cells, such as human breast carcinoma MCF-7 cells, induces the expression of a group of genes that comprise a cohort of retinoid-inducible genes. Several of these genes are growth-inhibitory genes, i.e., genes whose expression inhibits the growth or tumorigenicity of tumor cells. These genes are important, inter alia, as targets to be induced in tumor cells and other cells that proliferate inappropriately or pathogenically to inhibit the growth thereof. It was known in the art that genes whose expression was regulatable by retinoids contained a specific class of sequences in their promoters, termed RARE (Mangelsdorf et al., 1994, in The Retinoids: Biology, Chemistry, and Medicine, (Sporn et al., eds.), pp. 327–330 (Raven Press, New York). Surprisingly, however, all but one of the genes most strongly induced by retinoids in MCF-7 cells as determined by the inventors did not contain such RARE sequences in their promoters. This unexpected result indicated that retinoids activate these genes indirectly, by a mechanism that does not require RXR homodimer or RAR-RXR heterodimer binding to RARE sequences for these genes. This result also suggested that compounds other than retinoids should be capable of inducing expression of these (and perhaps other) growth-inhibitory genes in both retinoid-sensitive and retinoid-insensitive cells. Before the present invention, there was no reason to suspect that retinoid-insensitive cells could be induced to express retinoid-inducible growth inhibitory genes.

Disclosed herein is the inventors' discovery of 13 retinoid-inducible genes, including several genes having growth-inhibitory effects in mammalian cells. One of ordinary skill will appreciate that these results are not exhaustive, and other growth inhibitory genes may be induced by retinoids in mammalian cells. In view of the instant results, the skilled worker will also appreciate that some of these additional genes will be expected to lack RARE sequences in their promoters and thus be indirectly induced by retinoids. As disclosed herein, retinoid-inducible genes lacking RARE sequences in their promoters are useful targets for identifying compounds other than retinoids that mimic the physiologically-based growth inhibitory effect on cell proliferation. Identifying such compounds advantageously provides alternative agents for producing growth arrest in mammalian cells, particularly tumor cells and other cells that proliferate inappropriately or pathogenically. Such compounds are beneficial because they can mimic the growth-inhibitory effects of retinoids.

Another advantage of such compounds is that they can be expected to have a growth-inhibitory effect without producing systemic side effects found with other growth-inhibitory compounds known in the prior art. For example, many growth-inhibitory drugs and compounds known in the prior art disadvantageously induce p21 gene expression, which induces senescence, growth arrest and apoptosis by activating a plurality of genes, the expression of which is associated with the development of diseases, particularly age-related diseases such as Alzheimer's disease, atherosclerosis, renal disease, and arthritis (as disclosed in co-owned and co-pending U.S. Ser. No. 60/265,840, filed Feb. 1, 2001 and U.S. Ser. No. 09/861,925, filed May 21, 2001, incorporated by reference herein, Retinoic acid-induced growth inhibition in MCF-7 cells, in contrast, does not induce p21 (Zhu et al., 1997, Exp. Cell Res. 234:293–299). The genes identified herein that are induced by retinoids are not known to be associated with any disease or disadvantageous or pathogenic effect when expressed in an animal. Thus, identification of such compounds that mimic the growth-inhibitory effects of retinoids by inducing expression of one or a plurality of the genes identified herein can be expected to have reduced or no such side-effects, making them better agents for anti-tumor and other therapies. Discovery of compounds that mimic the growth-inhibitory effects of retinoids without producing the toxic side effects of growth-inhibitory compounds known in the art is thus advantageously provided by the invention.

As provided herein, mammalian genes responsive to retinoids but not containing RARE sites in their promoters include human insulin-like growth factor binding protein-3 (IGFBP-3; NCBI Accession No. M35878.1), secreted cell adhesion protein βIG-H3 (Accession No. AC004503.1), epithelial protein lost in neoplasm (EPLIN; Accession No. AH009382.1), ubiquitin-like protein FAT10 (Accession No. AL031983), Mac-2 binding protein (Mac-2 BP; Accession No. U91729), protein C inhibitor (PCI; Accession No. AL049839.3), T cell receptor gamma (Accession No. AC006033.2), retinal oxidase (Accession No. AF010260), Bene (Accession No. AP001234.3), HIF-2alpha/EPAS-1 (Accession No. NT_005065.3), selectin L (Accession No. AL021940.1), or proteasome activator PA28 subunit α (PA28α; Accession No. AL136295.2).

For the purposes of this invention, reference to "a cell" or "cells" is intended to be equivalent, and particularly encompasses in vitro cultures of mammalian cells grown and maintained as known in the art.

For the purposes of this invention, reference to "cellular genes" in the plural is intended to encompass a single gene as well as two or more genes. It will also be understood by those with skill in the art that effects of modulation of cellular gene expression, or reporter constructs under the transcriptional control of promoters derived from cellular genes, can be detected in a first gene and then the effect replicated by testing a second or any number of additional genes or reporter gene constructs. Alternatively, expression of two or more genes or reporter gene constructs can be assayed simultaneously within the scope of this invention.

As used herein, the term "RARE site" is intended to encompass two hexameric core motifs (as defined in Mangelsdorf et al., 1994, in THE RETINOIDS: BIOLOGY, CHEMISTRY, AND MEDICINE, (Sporn et al., eds.), pp. 327–330 (Raven Press, New York), separated by one, two or five nucleotides), wherein the hexameric motifs are arranged as direct, inverted or palindromic repeats.

The instant inventors have shown that treatment of MCF-7 human breast carcinoma cells with low doses of retinoids induces gradual growth arrest with minimal cytotoxicity and phenotypic features of cell senescence (Chang et al., 1999, Cancer Res. 59: 3761–3767). Relatively low doses of RA were found to induce irreversible growth arrest in MCF-7 cells, while producing only a minor reduction in cell numbers caused by cell death. This effect with "low dose" RA (between 10–100 nM) required 4–6 days of continuous exposure to RA to become apparent. Low-dose retinoid treatment was accompanied by the development of phenotypic changes in the treated cells characteristic for cellular senescence, including the development of an enlarged, flattened cellular morphology and expression of the senescence-associated marker, SA-β-galactosidase (SA-β-gal). Induction of SA-β-gal was also observed in xenografts of MCF-10T neo mammary epithelial cells in vivo after treatment with fenretinide. These results suggested that retinoid treatment induces senescence in tumor cells in vivo and in vitro when administered in cytostatic doses.

Senescence can be induced in a mammalian cell in a number of ways known to those with skill in the art. For example, senescence is a natural consequence of normal cell growth, either in vivo or in vitro: there are a limited number of cell divisions, passages or generations that a normal cell can undergo before it becomes senescent. The precise number varies with cell type and species of origin (Hayflick & Moorhead, 1961, Exp. Cell Res. 25: 585–621). Senescence can also be induced in both normal and tumor cells by treatment with cytotoxic drugs such as most anticancer drugs or radiation. See, Chang et al., 1999, Cancer Res. 59: 3761–3767. Senescence also can be rapidly induced in any mammalian cell by transducing into that cell a tumor suppressor gene (such as p53, p21, p16 or Rb) and expressing the gene therein. See, Sugrue et al., 1997, Proc. Natl. Acad. Sci. USA 94: 9648–9653; Uhrbom et al., 1997, Oncogene 15: 505–514; Xu et al., 1997, Oncogene 15: 2589–2596; Vogt et al., 1998, Cell Growth Differ. 9: 139–146. These and other means and methods for inducing senescence in mammalian cells will be appreciated and understood by those with skill in the art, and fall within the compass of this invention.

The reagents of the present invention include any mammalian cell, preferably a rodent or primate cell, more preferably a mouse cell and most preferably a human cell, that can induce cellular gene expression in response to a retinoid, wherein such gene is either the endogenous gene or an exogenous gene introduced by genetic engineering. Preferred cells include mammalian cells, preferably rodent or primate cells, and more preferably mouse or human cells.

Recombinant expression constructs can be introduced into appropriate mammalian cells as understood by those with skill in the art. Preferred embodiments of said constructs are produced in transmissible vectors, more preferably viral vectors and most preferably retrovirus vectors, adenovirus vectors, adeno-associated virus vectors, and vaccinia virus vectors, as known in the art. See, generally, MAMMALIAN CELL BIOTECHNOLOGY: A PRACTICAL APPROACH, (Butler, ed.), Oxford University Press: New York, 1991, pp. 57–84.

The invention also provides recombinant expression constructs wherein a reporter gene is under the transcriptional control of a promoter of a gene whose expression is induced by a retinoid. In preferred embodiments of this aspect of the invention, the retinoid is all-trans retinoic acid, fenretinide, 9-cis retinoic acid, 13-cis retinoic acid, etretinate or retinol. In preferred embodiments, the promoters are derived from genes whose expression is induced or otherwise increased by treatment of the cell with a retinoid, and preferably from human insulin-like growth factor binding protein-3 (IGFBP- 3; SEQ ID NO. 1), secreted cell adhesion protein βIG-H3 (SEQ ID NO. 2), epithelial protein lost in neoplasm (EPLIN; SEQ ID NO. 3), ubiquitin-like protein FAT10 (SEQ ID NO. 4), proteasome activator PA28 subunit α (PA28α; SEQ ID NO.:5), Mac-2 binding protein (Mac-2 BP; SEQ ID NO.:6), Protein C inhibitor (PCI; SEQ ID NO.:7), T cell receptor gamma (SEQ ID NO.:8), retinal oxidase (SEQ ID NO.:9), Bene (SEQ ID NO.:10), HIF-2alpha/EPAS-1 (SEQ ID NO.:11), or selectin L (SEQ ID NO.: 12). Most preferably, the promoter is derived from human insulin-like growth factor binding protein-3 (IGFBP-3; SEQ ID NO. 1), secreted cell adhesion protein βIG-H3 (SEQ ID NO. 2), epithelial protein lost in neoplasm (EPLIN; SEQ ID NO. 3), ubiquitin-like protein FAT10 (SEQ ID NO. 4), or proteasome activator PA28 subunit α (PA28α; SEQ ID NO.:5), Mac-2 binding protein (Mac-2 BP; SEQ ID NO.:6), Protein C inhibitor (PCI; SEQ ID NO.:7), T cell receptor gamma (SEQ ID NO.:8), retinal oxidase (SEQ ID NO.:9), Bene (SEQ ID NO.: 10), HIF-2alpha/EPAS-1 (SEQ ID NO.:11), or selectin L (SEQ ID NO.:12). Most preferably, the promoter is derived from human insulin-like growth factor binding protein-3 (IGFBP-3; SEQ ID NO. 1), secreted cell adhesion protein βIG-H3 (SEQ ID NO. 2), epithelial protein lost in neoplasm (EPLIN; SEQ ID NO. 3), ubiquitin-like protein FAT10 (SEQ ID NO. 4), or proteasome activator PA28 subunit α (PA28α; SEQ ID NO. 5). These reporter genes are then used as sensitive and convenient indicators of the effects of retinoid-induced gene expression, and enable compounds that mimic the effects of retinoids in mammalian cells to be easily identified. Host cells for these constructs include any mammalian cell. Reporter genes useful in the practice of this aspect of the invention include but are not limited to firefly luciferase, chloramphenicol acetyltransferase, beta-galactosidase, green fluorescent protein, and alkaline phosphatase.

The following Examples are intended to further illustrate certain preferred embodiments of the invention and are not limiting in nature.

EXAMPLE 1

Analysis of Gene Expression Modulation by Treatment with Retinoic Acid

Cytological and gene expression analyses were performed to determine the effects of retinoic acid treatment on MCF-7 cells in culture.

Clonogenic assays were performed to analyze the differences in proliferative capacity in MCF-7 cells after treatment with 100 nM RA for varying times. Cells were exposed to 100 nM RA for 1–7 days and tested for their capacity to form colonies after treatment at each time point. As shown in FIG. 1A, plating efficiency, normalized to untreated control, decreased with time of cell incubation with 100 nM RA. The decrease was initially rapid (from 100% to 40% plating efficiency after 2 days incubation with RA) and decreased more slowly to a final plating efficiency of about 10% at day 7. FIG. 1B shows the plating efficiency of MCF-7 cells at varying concentrations of RA; these results show a dose-dependent reduction in plating efficiency at all tested doses (as low as 10 nM). Significant reduction in plating efficiency was observed at concentrations much lower than conventionally used ($\geq 1 \mu M$) to study the effects of retinoids on cell growth.

These results were consistent with a reduction in cell growth and proliferative capacity due to retinoid-modulated changes in cellular gene expression. To study gene expression changes, poly(A)+ RNA was isolated from untreated MCF-7 cells and from cells treated for 5 days with 100 nM RA. cDNA was prepared from these RNA populations and the cDNA hybridized with a cDNA microarray (Human UniGEM V cDNA microarray, Incyte Genomics, St. Louis, Mo.) that contains >7,000 cDNAs of different human genes and ESTs. cDNA probe synthesis, hybridization with the microarray and signal analyses were conducted by Incyte-Genomics as a commercial service.

None of the genes in the microarray showed an increase in relative hybridization intensity over 2.5-fold or a decrease over 3-fold in RA-treated cells. Changes in RNA levels of a total of 47 genes that showed the biggest differences in microarray hybridization were tested by reverse transcription-PCR (RT-PCR) analysis. Of these, 27 genes showed 1.4–2.5 fold increase and 20 genes showed 1.7–3.0 fold decrease in 'balanced differential expression' (a measure of relative hybridization intensity).

RT-PCR analysis was carried out essentially as described (Noonan et al., 1990, *Proc. Natl. Acad. Sci. USA* 87: 7160–7164), using β-actin as an internal normalization standard. Sequences of RT-PCR primers and PCR conditions for thirteen genes most strongly induced by RA are as follows:

TABLE I

Oligonucleotide primers for performing PCR

| Gene | Sense Primer (5'□3') | | Antisense Primer (5'□3') | |
|---|---|---|---|---|
| IGFBP-3 | TTGCACAAAAGACTGCCAAG | (SEQ ID NO:14) | CATGAAGTCTGGGTGCTGTG | (SEQ ID NO.:15) |
| Mac-2 BP | AATTCCACACTGTGCCCTTC | (SEQ ID NO.:16) | GTGGAGTCTGGAAGGACTGG | (SEQ ID NO.:17) |
| beta IG-H3 | TGCGACTAGCCCCTGTCTAT | (SEQ ID NO.:18) | CATGCACAAGGCTCACATCT | (SEQ ID NO.:19) |
| PCI | GCACCCAAGAGCAAGACTTC | (SEQ ID NO.:20) | CGAGCTGCCTCTTTTTGAAC | (SEQ ID NO.:21) |
| FAT 10 | AATGCTTCCTGCCTCTGTGT | (SEQ ID NO.:22) | ATCACTGGGCTTCACCACTT | (SEQ ID NO.:23) |
| EPLIN beta | AGAAAGGGGACCCTGACTGT | (SEQ ID NO.:24) | AAGATCCTCACCGTCCTTGA | (SEQ ID NO.:25) |
| T cell receptor gamma | AGGAGCTGTGGAAAACATGG | (SEQ ID NO.:26) | CATAACAGACGGTGGCACAA | (SEQ ID NO.:27) |

TABLE I-continued

Oligonucleotide primers for performing PCR

| Gene | Sense Primer (5'□3') | | Antisense Primer (5'□3') | |
|---|---|---|---|---|
| P28 alpha | ACAGGTGGATGTGTTTCGTG | (SEQ ID NO.:28) | TTCATCCTCCCCCTTCTTCT | (SEQ ID NO.:29) |
| Retinal oxidase | GTGGTGGACATCATGACAGC | (SEQ ID NO.:30) | AGCGGCTCCAAGTCTTGATA | (SEQ ID NO.:31) |
| Bene | CCAGGCAACAAAAGGAGAGA | (SEQ ID NO.:32) | TGCCTTCTGTCATTGGGAAT | (SEQ ID NO.:33) |
| HIF-2alpha/EPAS-1 | CCAGTGCATCATGTGTGTCA | (SEQ ID NO.:34) | CCCGAAATCCAGAGAGATGA | (SEQ ID NO.:35) |
| L-selectin | GTGGCACCTCCTACGTCAAA | (SEQ ID NO.:36) | TGAATCCTTTCCCTTTATGGTC | (SEQ ID NO.:37) |
| RNF | GAGGTGCAGTCCAAAAGGAA | (SEQ ID NO.:38) | TGTGTTGGCGTACAGGTCTTTG | (SEQ ID NO.:39) |
| Beta-actin | TGTGTTGGCGTACAG-GTCTTTG | (SEQ ID NO.:40) | TGTGTTGGCGTACAGGTCTTTG | (SEQ ID NO.:41) |

TABLE II

Temperature conditions for PCR (in ° C.)

| Gene | Denaturation | Annealing | Extension | Cycles | Product size |
|---|---|---|---|---|---|
| IGFBP-3 | 95 | 60 | 72 | 27 | 247 |
| Mac-2BP | 95 | 60 | 72 | 29 | 249 |
| beta IG-H3 | 95 | 60 | 72 | 27 | 199 |
| PCI | 95 | 60 | 72 | 28 | 249 |
| FAT 10 | 95 | 60 | 72 | 27 | 246 |
| EPLIN beta | 95 | 60 | 72 | 26 | 261 |
| T cell receptor gamma | 95 | 60 | 72 | 26 | 252 |
| PA28 alpha | 95 | 60 | 72 | 27 | 250 |
| Retinal oxidase | 95 | 60 | 72 | 29 | 197 |
| Bene | 95 | 60 | 72 | 26 | 265 |
| HIF-2 alpha/EPAS-1 | 95 | 60 | 72 | 26 | 250 |
| L-selectin | 95 | 60 | 72 | 26 | 195 |
| RNF | 95 | 60 | 72 | 29 | 200 |
| beta actin | 95 | 60 | 72 | 21 | 275 |

Figure 2:
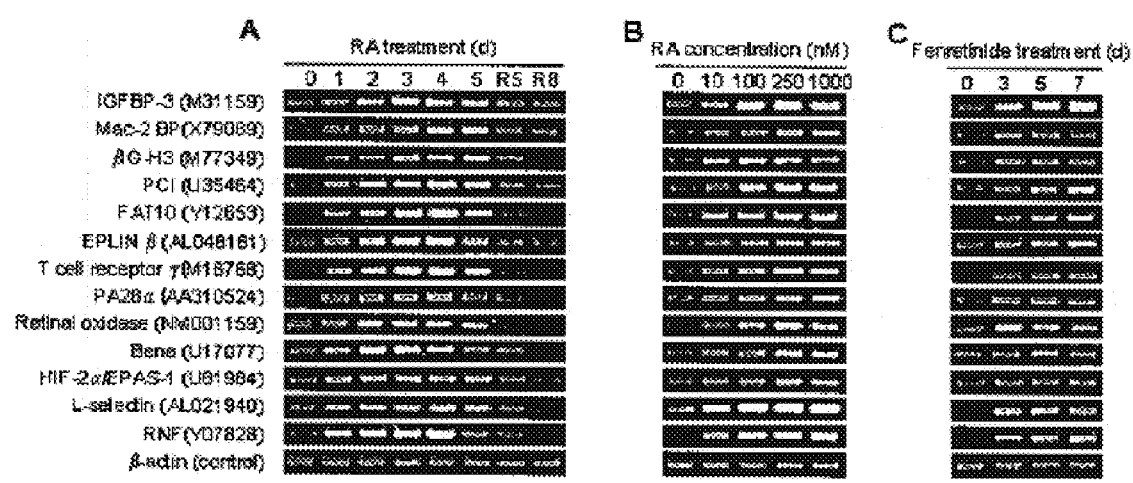
FIGS. 2A through 2C show the results of RT-PCR analysis of changes in the expression of retinoid-inducible genes as described in Example 1. The identity of each gene is followed by the NCBI Accession Number (in parentheses).

RT-PCR assays confirmed altered expression for 43 of 47 genes and showed that 13 upregulated genes were induced by RA much more strongly (5–10 fold or more) than indicated by microarray hybridization; these results are shown in FIGS. 2A and 2B. Time course analysis of changes in RNA levels of these 13 genes (FIG. 2A) showed that many of them increased their expression between days 1 and 4 of RA treatment, in parallel with the loss of clonogenicity (shown in FIG. 1A). Analysis of RA dose-dependence of gene expression (shown in FIG. 2B) showed that almost all of these genes were induced even by the lowest (10 nM) dose of RA that produced detectable loss of clonogenicity (shown in FIG. 1B). All 13 genes were also induced by treatment with 1 µM of another retinoid, fenretinide, which is used in breast cancer chemoprevention (these results are shown in FIG. 2C).

Figure 3:
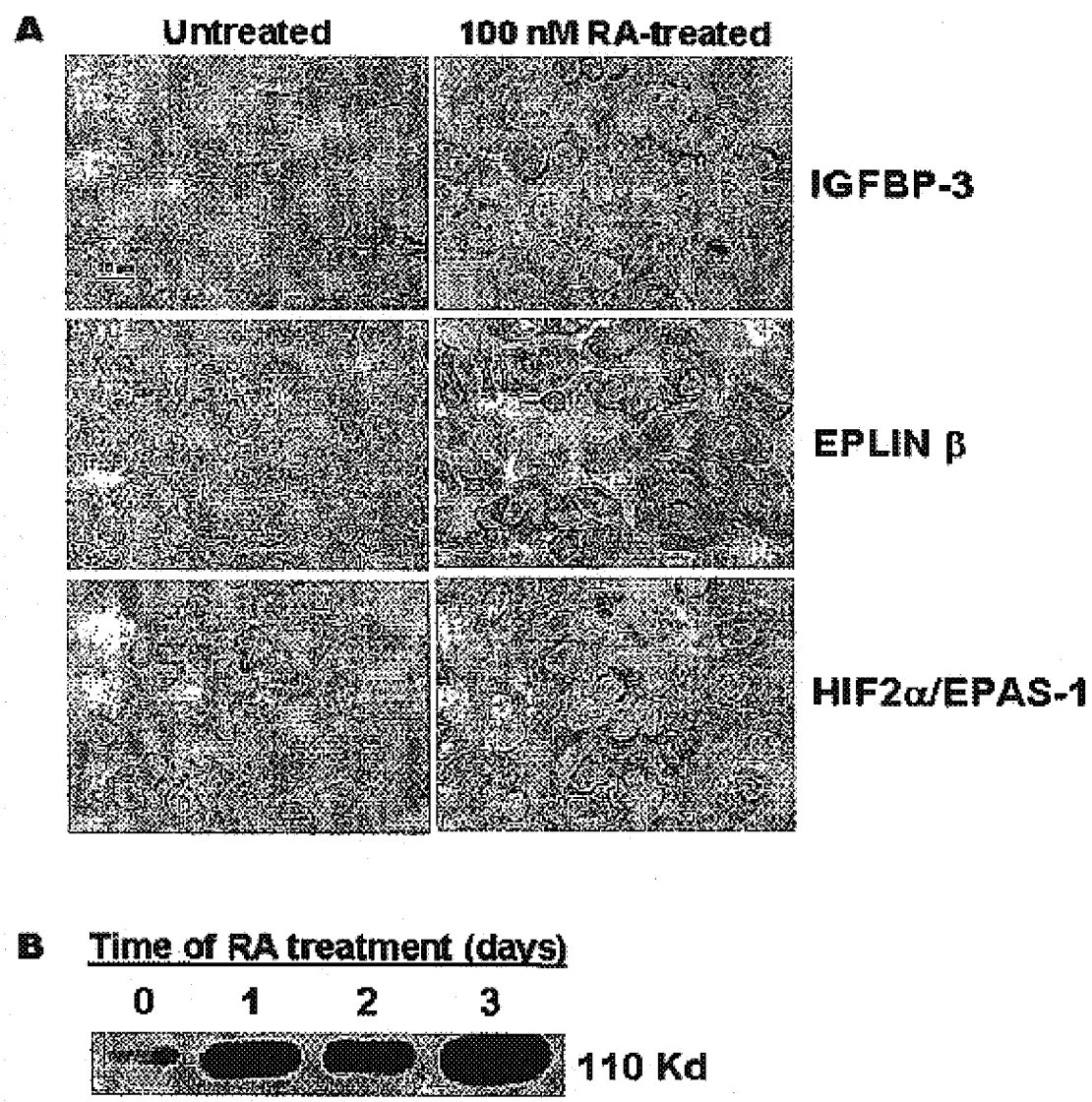
FIG. 3A is a photomicrograph and FIG. 3B is a photograph of an immunoblot showing induction of IGFBP-3, HIF2α/EPAS-1 and EPLIN proteins in RA-treated cells.

Induction of three genes in this group was tested and confirmed at the protein level, by immunocytochemical assays, shown in FIG. 3A, using rabbit polyclonal antibody against EPLIN (a gift of Dr. David Chang, UCLA), and goat polyclonal antibodies against IGFBP-3 and EPAS-1/HIF-2α (Santa Cruz Biotechnology, Inc., Santa Cruz, Calif.) and standard techniques. Antibody staining was detected using Vectastain kit (Vector Labs, Burlingame, Calif.) according to the manufacturer's instructions. These results show that induction of IGFBP-3, EPAS-1/HIF2α, and EPLIN mRNA was accompanied by increased expression of the corresponding proteins in RA-treated cells.

These results showed that RA and fenretinide strongly induced the expression of a common set of genes under the conditions where these retinoids inhibit cell growth and induce the senescent phenotype.

EXAMPLE 2

Biological Functions of Genes Induced in MCF-7 Cells by Treatment with Retinoic Acid The genes detected as discussed in Example 1 were found by literature research to have biological functions that are relevant to the cellular effects of retinoids.

Strikingly, 4 of 13 genes that are strongly induced by retinoids have been reported to possess antiproliferative activity. The first gene encodes insulin-like growth factor binding protein-3 (IGFBP-3), a secreted factor that was shown to be inducible by RA in breast carcinoma cells and to inhibit the growth of these cells (Adamo et al., 1992, *Endocrinology* 131: 1858–1866; Gucev et al., 1996, *Cancer Res.* 56: 1545–1550). In addition to its role in IGF sequestration, IGFBP-3 was recently found to bind and modulate the transcriptional activity of a retinoid receptor RXRα (Liu et al., 2000, *J Biol. Chem.* 275: 33607–33613). Induction of IGFBP-3 was confirmed by immunocytochemical assays shown in FIG. 3A.

Another growth-inhibitory gene induced by treatment with retinoids encodes secreted cell adhesion protein βIG-H3, which is inducible by TGF-β, in several cell types (Skonier et al., 1992, *DNA Cell Biol.* 11: 511–522). Transfection of βIG-H3 was shown to inhibit the tumorigenicity of Chinese hamster ovary cells (Skonier et al., 1994, *DNA*

*Cell Biol.* 13: 571–584). βIG-H3 is expressed in normal but not in neoplastically transformed human fibroblasts (Schenker & Trueb, 1998, *Exp.Cell Res.* 239: 161–168), suggesting that this gene may be a tumor suppressor.

The third gene encodes a LIM domain protein termed EPLIN, an actin-binding protein that is expressed in primary epithelial cells but downregulated in different types of carcinomas (Maul & Chang, 1999, *Oncogene* 18: 7838–7841). Ectopic expression of EPLIN was shown to suppress cell proliferation in an osteosarcoma cell line (Maul & Chang, Id.). The EPLIN gene encodes two protein isoforms, EPLINα and EPLINβ, with the larger (β) isoform showing a stronger growth-inhibitory effect. The observed induction of EPLIN gene expression was confirmed by immunocytochemical and immunoblotting assays (results shown in FIGS. 3A and 3B). These assays were performed using rabbit polyclonal antibody against EPLIN (a gift of Dr. David Chang, UCLA) and were carried out by standard techniques. Antibody staining was detected using Vectastain kit (Vector Labs) for immunocytochemistry and horseradish peroxidase-conjugated goat anti-rabbit IgG (Santa Cruz) for immunoblotting. Electrophoretic mobility of EPLIN in MCF-7 cells (110 kDa; FIG. 3B) corresponds to the β isoform, consistent with the art that showed stronger growth inhibition by this isoform.

The fourth gene encodes an ubiquitin-like protein FAT10. FAT10 interacts with a mitotic spindle protein Mad2, and its overexpression in HeLa carcinoma cells was reported to be detrimental to cell survival (Liu et al., 1999, *Proc. Natl. Acad. Sci. USA* 96: 4313–4318.

Retinoic acid treatment is known to promote proteasome-mediated degradation of retinoic acid receptor RARα (Zhu.et al., 1999, *Proc. Natl. Acad. Sci. USA* 96:14807–14812) and of cyclin D (Spinella et al., 1999, *J. Biol. Chem.* 274: 22013–22018). Proteasome-mediated cyclin D degradation has been proposed as a mechanism for retinoid-induced growth arrest (Spinella et al., Id.). Remarkably, one of the RA-induced genes encodes proteasome activator PA28 subunit α (PA28 α). Expression of PA28α is sufficient to activate the proteasome (Groettrup et al., 1996, *Nature* 381:166–168), and the induction of this gene may account at least in part for proteasome activation by retinoids. Pa28α therefore can be regarded as another growth inhibitor.

Still another RA-induced gene encodes retinal oxidase (aldehyde oxidase), an enzyme that catalyses the final step of RA synthesis from vitamin A (Huang et al., 1999, *Arch. Biochem. Biophys.* 364: 264–272). The observed induction of retinal oxidase suggests that retinoid treatment may stimulate RA synthesis in the treated cells, providing a potential positive feedback mechanism.

Aside from βIG-H3, two other induced genes encode secreted proteins that may contribute to the senescence-like flattened morphology and increased adhesion of RA-treated MCF-7 cells. One of these encodes Mac-2 binding protein (Mac-2 BP), a cell adhesion factor of the extracellular matrix (Sasaki et al., 1998, *EMBO J.* 17: 1606–1613). Mac-2 BP is also upregulated in p21-induced senescence of human fibrosarcoma cells (Chang et al., 2000, *Proc. Natl. Acad. Sci. USA* 97: 4291–4296). The other gene encodes protein C inhibitor (PCI), a non-specific serine protease inhibitor, which is normally produced by the liver. While retinoid-treated MCF-7 cells express markers of senescence, none of the genes that are strongly induced by RA in this cell line has been associated with epithelial cell differentiation. Two of the induced genes, however, encode transmembrane proteins specific for the hematopoietic lineage, including the leukocyte homing receptor L-selectin and T-cell receptor. Induction of these genes correlates with a well-documented differentiating effect of retinoids in hematopoietic malignancies (Warrell, 1997, ibid.). RA also induces another transmembrane protein, Bene, which has no known function.

The last two RA-induced genes encode known or putative transcriptional regulators. One of them is HIF-2α/EPAS-1, a member of a family of PAS domain transcription factors that mediate the effects of hypoxia and some other stress factors on gene expression (Semenza, 1999, *Annu. Rev. Cell. Dev. Biol.* 15: 551–578). Interestingly, IGFBP-3 is also one of the hypoxia-stimulated genes (Feldser et al., 1999, *Cancer Res.* 59: 3915–3918). Induction of HIF-2α/EPAS-1 was confirmed by immunocytochemical assays shown in FIG. 3A.

The final RA-induced gene encodes a ring finger protein RNF (accession number YO7828). While the RNF function is unknown, it shares 25–38% amino acid identity with a family of regulatory proteins, some of which have been implicated in retinoid response, senescence or differentiation. These include TIF1α, which functions as a ligand-dependent transcriptional coactivator of retinoid receptors (Le Douarin et al., 1995, *EMBO J.* 14: 2020–2033), as well as promyelocytic leukemia (PML) gene, which is fused with RARα in the t(15;17)translocation in PML (Kakizuka et al., 1991, *Cell* 66: 663–674). PML has been recently identified as a mediator of accelerated senescence induced by mutant RAS in human fibroblasts (Ferbeyre et al., 2000, *Genes Dev.* 14: 2015–2027). Another member of the same family is HERF1, which is required for terminal differentiation of erythroid cells (Harada et al., 1999, *Mol. Cell. Biol.* 19: 3808–3815). Interestingly, HERF1, RNF and FAT10 all map to the major histocompatibility locus on chromosome 6p21.3. This locus also contains the gene for RARα, which was reported to be induced by RA (Shang et al., 1999, *J. Biol. Chem.* 274:18005–18010) and to be upregulated in senescent mammary cells (Swisshelm et al., 1994, *Cell Growth Differ.* 5: 133–141).

As disclosed herein, retinoid treatment of breast carcinoma cells concurrently induces several genes with known antiproliferative functions, including candidate tumor suppressors that are selectively downregulated in neoplastic cells (EPLIN and βIG-H3). Since the UniGem V array comprises only a fraction of all human genes, the actual number of growth inhibitors that are co-induced by retinoids should be much higher than the genes identified herein. Such additional retinoid-inducible growth inhibitors can be readily identified, however, by hybridizing cDNA probes described herein with larger cDNA arrays or combinations of arrays, or by carrying differential cDNA cloning using methods that are well known in the art (see, for example, International Patent Application, Publication No. WO00/61751, incorporated by reference herein.

These results demonstrated that retinoids can induce several growth-inhibitory genes, which provide a basis for developing reagents for screening compounds capable of inducing one or more of these genes without producing retinoid-associated resistance or toxicity.

EXAMPLE 3

Construction of Retinoid-Regulated Promoter-Reporter Gene Constructs that Are Induced with Retinoic Acid In order to produce reporter gene constructs under the transcriptional control of retinoid-induced genes, promoter sequences for all 13 genes that are strongly induced by retinoids, comprising 1400–1500 bp upstream of the 5' end of the longest available cDNA sequence of the respective genes, were identified in the human genome database.

These sequences were then analyzed for the presence of two closely spaced hexameric core motifs of RARE sites (Mangelsdorf et al., 1994, in THE RETINOIDS: BIOLOGY, CHEMISTRY, AND MEDICINE, (Sporn et al., eds.), pp. 327–330 (Raven Press, New York), in variable orientations, using the "Regulatory Sequence Analysis Tools" available from the University of Brussels, Belgium.

A putative RARE site found in only one promoter, ring finger protein RNF, where the sequence:

AGGTCACAGCCAGTTCA (SEQ ID No.:42)

(boldface indicates the RARE core motifs; Mangelsdorf et al., 1994, ibid.) appears in inverse orientation about 360 bp upstream of the apparent transcription start site. None of the other promoters contained discernable RARE sequences, suggesting that most of these genes are induced by retinoids through indirect mechanisms. Interestingly, RNF is also the only gene in this group to reach its maximum expression after just one day of treatment (see FIG. 2A), suggesting that RNF is likely to be directly inducible by retinoids.

It is remarkable that none of the growth-inhibitory genes that show strong and sustained induction in RA-treated MCF-7 cells contain RARE sites in their promoters, suggesting that it may be possible to induce these growth-inhibitory genes in cells that lack retinoid receptors, and using non-retinoid inducing agents. Reporter gene-containing constructs, under the transcriptional control of a promoter from a retinoid-induced gene, particularly a gene lacking a RARE sequence in the promoter, enable screening of test compounds for the capacity to induce gene expression from these genes in a way that mimics the gene-inducing effects of retinoids without producing toxicity or development of resistance.

Such reporter gene constructs are prepared as follows. The promoter region of a retinoid-regulated gene, such as βIG-H3, is identified in the genomic sequence (NCBI accession number AC004503) as adjacent to the 5' end of the cDNA. Polymerase chain reaction (PCR) amplification of the promoter-specific DNA is performed using genomic DNA from human MCF-7 cells as the template and the following primers for βIG-H3:

```
5' GGCCAGGTGCCTCTTCTTAG 3' (sense)  (SEQ ID NO.:43)
and
5' CGGCTCCAGGGAAGTGAG 3'   (anti-   (SEQ ID NO.:44)
                           sense)
``` using PfuTurbo DNA Polymerase (Stratagene) and 28 cycles of PCR where each cycle consisted of 45 sec. at 95° C., 1 min 30 sec. at 60° C., and 2 min. at 72° C. A 1020 bp fragment is amplified using this method and cloned into the TOPO TA cloning vector pCRII/TOPO (Invitrogen). The sequence identity of this construct is verified, and the HindIII-Xho I fragment containing the promoter in the correct orientation is then inserted into the HindIII and Xho I sites in a firefly luciferase-reporter vector pGL2-Basic (Promega, Madison, Wis.) using standard recombinant genetic techniques (Sambrook et al., 1990, Molecular Cloning: A Laboratory Manuel, Cold Spring Harbor Laboratory Press: New York).

The ability of this construct to drive retinoid-inducible luciferase expression in mammalian cells is demonstrated in transient transfection assay, as described in U.S. Provisional Patent Application Serial No. 60/265,840, filed Feb. 1, 2001 and U.S. patent application Ser. No. 09/861,925, filed May 21, 2001, incorporated by reference herein. Briefly, transfection is carried out using LIPOFECTAMINE 2000 (Life Technologies, Inc. Gaithersburg). Cells are plated at a density of 70,000 cells/well in 12 well plates in 1 ml media containing 2 mM glutamine, 10% FBS; 0.1 mM NEAA (Non-Essential Amino Acids, GIBCO), 1 mM sodium pyruvate, and 10 μg/mL insulin, and without penicillin/streptomycin. After culturing the cells for a sufficient time that they attached to the culture dish, transfection was performed in triplicate according to the manufacturer's instructions, using 1 μg pGL2-basic vector DNA and 1 μg pGL2-βIG-H3 promoter DNA. After 10 hours, culture media is replaced with media containing penicillin/streptomycin at standard tissue culture concentrations. The cells were then incubated in the presence or absence of 100 nM atRA for 72 hours. After incubation, cells are washed twice with phosphate-buffered saline and collected in 100 μL of Reporter Lysis Buffer (Promega). The lysate is left at room temperature for 10 minutes followed by 1 cycle of freeze/thaw using a dry ice-ethanol bath for freezing the cell sample and thawing in a 37° C. water bath. 50 μL aliquots are transferred to fresh tubes for Firefly Luciferase Assay (Promega). Luciferase activity is measured as described above using a Turner 20/20 luminometer at 47.9% sensitivity with a 5 sec. delay period and 15 sec. integration time. An additional aliquot is removed from the cell lysate to measure protein concentration using Bio-Rad protein assay kit (Bradford assay). Luciferase activity for each sample is normalized to protein content and expressed as luciferase/μg protein. All assays are carried out in triplicate and displayed as a mean and standard deviation.

To develop a stably transfected cell line with retinoid-regulated luciferase expression, the construct described above is introduced into a cell line that is susceptible to growth inhibition by retinoids, such as MCF7 cells by cotransfection with a vector encoding a selectable marker, such as pBabePuro, carrying puromycin N-acetyltransferaseas a selectable marker. Transfection is carried out using LIPOFECTAMINE 2000 (Life Technologies, Inc., Gaithersburg, Md.), using a 10:1 ratio of the construct and a plasmid or other vector containing a selectable marker. Stable transfectants are selected using an appropriate amount of a selecting agent specific for the selectable marker encoded by the plasmid or vector. Selective agent-resistant cell lines are isolated and tested for luciferase activity (using a Luciferase Assay System, Promega), in the presence and in the absence of 100 nM RA, or another retinoid at a concentration that produces growth inhibition in the recipient cell line.

This assay is performed as follows. Cells are plated at a density of 40,000 cells/well in 12 well plates in 1 mL of media containing penicillin/streptomycin, glutamine and 10% fetal calf serum (FCS). After attachment, cells are treated with 100 nM RA or left untreated for different periods of time. Cells are washed twice with phosphate-buffered saline and collected in 300 μL of Reporter Lysis Buffer (RLB; Promega). The lysate is centrifuged briefly at 10,000 g to pellet debris, and 50 μL aliquots are transferred to fresh tubes for use in the Firefly Luciferase assay (Promega). Luciferase activity is measured using a Turner 20/20 luminometer at 55.6% sensitivity with a 5 second delay period and 15 second integration time. An additional aliquot is removed from the cell lysate to measure protein concentration using the Bio-Rad protein assay kit (Bradford assay). Luciferase activity for each sample is normalized to protein content and expressed as luciferase activity/µg protein. All assays are carried out in triplicate and displayed as a mean and standard deviation.

Such constructs and cells provide a basis for a screening assay for identifying compounds that induce retinoid-induced gene expression. The same type of screening can also be conducted using transient transfection assays with promoter constructs of retinoid-inducible genes rather than stably-transfected cell lines. The methods for high-throughput screening based on luciferase expression are well known in the art (see Storz et al., 1999, *Analyt. Biochem.* 276: 97–104 for a recent example of a transient transfection-based assay and Roos et al., 2000, *Virology* 273: 307–315 for an example of screening based on a stably transfected cell line). Compounds identified using these cells and assays are in turn useful for developing therapeutic agents that can induce gene expression of retinoid-inducible genes without the concomitant toxicity or tendency to produce retinoid resistance.

The absence of retinoid responsive elements in the promoters of almost all of the genes shown herein to be induced by retinoid treatment of MCF-7 cells also suggests that compounds other than retinoids can be screened for their capacity to induce retinoid-inducible gene expression in the absence of retinoids or in cells lacking retinoid receptors. Such screening assays are performed as follows. A recombinant expression construct, prepared as described above and verified for inducibility by retinoids, is introduced by transfection into any mammalian cell line, whether sensitive or insensitive to retinoids, for example HT1080 cells (A.T.C.C. Accession No. CCL121) that are known to lack retinoic acid receptors. Stable transfectants are selected as described above using an appropriate amount of a selecting agent specific for the selectable marker encoded by the plasmid or vector, and selective agent-resistant cell lines are isolated thereby.

These cells are used in luciferase activity assays (using a Luciferase Assay System, Promega) as described above. These assays are performed on cells cultured in the presence or absence of increasing amounts of the compound to be tested for different periods of time, or cultured in compound-free media.

This assay is performed substantially as described above. Cells are plated at a density of 40,000 cells/well in 12 well plates in 1 mL of media containing penicillin/streptomycin, glutamine and 10% fetal calf serum (FCS). After attachment, cells are treated with increasing concentration of a compound to be tested, or left untreated for different periods of time. Cells are washed with PBS, collected in 300 µL RLB, centrifuged briefly to remove debris, and then assayed as above using the Firefly Luciferase assay. Protein concentrations are determined to normalize the luciferase results, which are expressed as luciferase activity/µg protein. All assays are carried out in triplicate and displayed as a mean and standard deviation. Finally, cells are assayed in parallel for growth inhibition by the tested compound using cell counting or measuring cell number after staining with MTT (3-(4,5-dimethylthiazol-2-yl)-2,5-diphenyltetrazolium bromide), methylene blue or other cell-specific stain It should be understood that the foregoing disclosure emphasizes certain specific embodiments of the invention and that all modifications or alternatives equivalent thereto are within the spirit and scope of the invention as set forth in the appended claims.

We claim:

1. A method for identifying a non-retinoid compound that induces expression of a retinoid-inducible gene in a mammalian cell, the method comprising the steps of:
   (a) culturing a recombinant mammalian cell in the presence and absence of a compound, wherein the recombinant mammalian cell comprises a recombinant expression construct encoding a reporter gene operably linked to a promoter from a gene the expression of which is induced by a retinoid, wherein the promoter does not contain a RARE site;
   (b) comparing reporter gene expression in said cell in the presence of the compound with reporter gene expression in said cell in the absence of the compound; and
   (c) identifying the compound that induces retinoid-induced gene expression if reporter gene expression is higher in the presence of the compound than in the absence of the compound.

2. The method of claim 1, wherein expression of the reporter gene is detected using an immunological reagent.

3. The method of claim 1, wherein expression of the reporter gene is detected by assaying for an activity of the reporter gene product.

4. The method of claim 1, where expression of the reporter gene is detected by hybridization to a complementary nucleic acid.

* * * * *